(12) United States Patent
Praszczalek et al.

(10) Patent No.: US 11,843,599 B2
(45) Date of Patent: Dec. 12, 2023

(54) SYSTEMS, METHODS, AND NON-TRANSITORY COMPUTER-READABLE MEDIA FOR SECURE BIOMETRICALLY-ENHANCED DATA EXCHANGES AND DATA STORAGE

(71) Applicant: MASTERCARD INTERNATIONAL INCORPORATED, Purchase, NY (US)

(72) Inventors: Przemek Praszczalek, Irvington, NY (US); Raman Narayanswamy, Nashua, NH (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 307 days.

(21) Appl. No.: 17/232,970

(22) Filed: Apr. 16, 2021

(65) Prior Publication Data
US 2021/0328982 A1    Oct. 21, 2021

Related U.S. Application Data

(60) Provisional application No. 63/011,185, filed on Apr. 16, 2020.

(51) Int. Cl.
| | | |
|---|---|---|
| *H04L 29/06* | (2006.01) | |
| *H04L 9/40* | (2022.01) | |
| *G06F 16/23* | (2019.01) | |
| *G06F 21/45* | (2013.01) | |
| *G16H 10/60* | (2018.01) | |

(Continued)

(52) U.S. Cl.
CPC ...... *H04L 63/0861* (2013.01); *G06F 16/2379* (2019.01); *G06F 21/45* (2013.01); *G06Q 40/08* (2013.01); *G16H 10/60* (2018.01); *H04L 9/3213* (2013.01); *H04L 9/3231* (2013.01)

(58) Field of Classification Search
CPC . H04L 63/0861; H04L 9/3213; H04L 9/3231; H04L 9/0894; H04L 9/12; H04L 63/0407; G06F 16/2379; G06F 21/45; G06F 16/9566; G06Q 40/08; G16H 10/60
See application file for complete search history.

(56) References Cited

U.S. PATENT DOCUMENTS

| | | |
|---|---|---|
| 5,280,527 A | 1/1994 | Gullman et al. |
| 10,515,419 B1 | 12/2019 | Walker et al. |

(Continued)

FOREIGN PATENT DOCUMENTS

| | | |
|---|---|---|
| WO | 2001017310 A1 | 3/2001 |
| WO | 2016/128906 A1 | 8/2016 |

OTHER PUBLICATIONS

International Search Report and Written Opinion for Application No. PCT/US2021/027706 dated Jul. 28, 2021 (9 pages).

(Continued)

*Primary Examiner* — Mahfuzur Rahman
(74) *Attorney, Agent, or Firm* — Michael Best & Friedrich LLP

(57) ABSTRACT

A privacy-enhancing system, method, and non-transitory computer-readable medium for securely identifying or verifying an individual over time without retaining sensitive biometric data (e.g., biometric images or biometric templates) for the purpose of securely storing data regarding the individual.

20 Claims, 22 Drawing Sheets

(51) Int. Cl.
*G06Q 40/08* (2012.01)
*H04L 9/32* (2006.01)

(56) References Cited

U.S. PATENT DOCUMENTS

| | | | |
|---|---|---|---|
| 10,572,641 B1* | 2/2020 | Griffin | ................. H04L 9/3239 |
| 2004/0234117 A1 | 11/2004 | Tibor | |
| 2008/0313726 A1* | 12/2008 | Gardner | ................ H04L 9/3273 |
| | | | 726/9 |
| 2013/0166450 A1 | 6/2013 | Pama | |
| 2014/0289824 A1 | 9/2014 | Chan et al. | |
| 2016/0241403 A1 | 8/2016 | Lindemann | |
| 2017/0039568 A1 | 2/2017 | Tunnell et al. | |
| 2017/0264599 A1 | 9/2017 | O'Regan et al. | |
| 2018/0198614 A1 | 7/2018 | Neumann | |
| 2020/0145219 A1 | 5/2020 | Sebastian et al. | |
| 2020/0226285 A1 | 7/2020 | Bulleit et al. | |
| 2020/0380520 A1 | 12/2020 | Kavali | |

OTHER PUBLICATIONS

International Search Report and Written Opinion for Application No. PCT/US2021/027745 dated Jul. 28, 2021 (10 pages).

* cited by examiner

SYSTEMS, METHODS, AND NON-TRANSITORY COMPUTER-READABLE MEDIA FOR SECURE BIOMETRICALLY-ENHANCED DATA EXCHANGES AND DATA STORAGE

CROSS-REFERENCE TO RELATED APPLICATIONS

This application claims the benefit of U.S. Provisional Application No. 63/011,185, filed on Apr. 16, 2020 , the entire content of which is hereby incorporated by reference.

FIELD OF THE INVENTION

The present disclosure relates generally to secure data exchanges or data storage. More specifically, the present disclosure relates privacy-enhancing systems, methods, and non-transitory computer-readable media with biometrically-enhanced data exchanges or storage.

BACKGROUND

A digital identification and personal data exchange improve privacy and security of individual's data which is accesses, shared, and exchanged between various individuals and entities. In particular, a digital identification and personal data exchange will help prevent unauthorized actors from assuming identities or gaining access to personal data of individuals. Use of digital identity service and data exchange service will also help facilitate new, innovative approaches to digital payments, commerce and financial inclusion.

The digital verification and identification as described herein is referred to as "Inclusive Verification of Identity." The following are aspects of a successful implementation of Inclusive Verification of Identity and Personal Data Exchange.

SUMMARY

A partner-specific identification Digital identification and personal data exchange will help in addressing the aftermath of the COVID-19 pandemic. In particular, a digital identification and personal data exchange will help prevent or counter nefarious actors from assuming identities or gaining access to personal data of victims of the COVID-19 pandemic. Use of digital identity service and data exchange service will also help facilitate new, innovative approaches to digital payments, commerce and financial inclusion.

One embodiment of the present disclosure includes a system for securely storing information of an individual. The system includes a local partner device that includes a first electronic processor, a first communication interface, and a first memory. The first electronic processor is configured to receive biometrics and registration information of an individual, generate, with a tokenization algorithm, a first biometric token based on the biometrics that are received, and create a data account associated with the individual in the first memory, the data account including the registration information and the first biometric token. The first biometric token is different from a biometric image or a biometric template in that the first biometric token only matches a copy of the first biometric token or a second biometric token that is generated from a second set of the biometrics of the individual with the tokenization algorithm.

Another embodiment of the present disclosure includes a method for securely storing information of an individual. The method includes receiving, with a local partner device, biometrics and registration information of an individual. The method includes generating, with the local partner device and a tokenization algorithm, a first biometric token based on the biometrics that are received. The method also includes creating, with the local partner device, a data account associated with the individual in a memory, the data account including the registration information and the first biometric token. The first biometric token is different from a biometric image or a biometric template in that the first biometric token only matches a copy of the first biometric token or a second biometric token that is generated from a second set of the biometrics of the individual with the tokenization algorithm.

Yet another embodiment of the present disclosure includes a non-transitory computer-readable medium comprising instructions that, when executed by an electronic processor, causes the electronic processor to perform a set of operations. The set of operations includes receiving, with a local partner device, biometrics and registration information of an individual. The set of operations includes generating, with the local partner device and a tokenization algorithm, a first biometric token based on the biometrics that are received. The set of operation also includes creating, with the local partner device, a data account associated with the individual in a memory, the data account including the registration information and the first biometric token. The first biometric token is different from a biometric image or a biometric template in that the first biometric token only matches a copy of the first biometric token or a second biometric token that is generated from a second set of the biometrics of the individual with the tokenization algorithm.

DETAILED DESCRIPTION OF THE EMBODIMENTS

Figure 1:
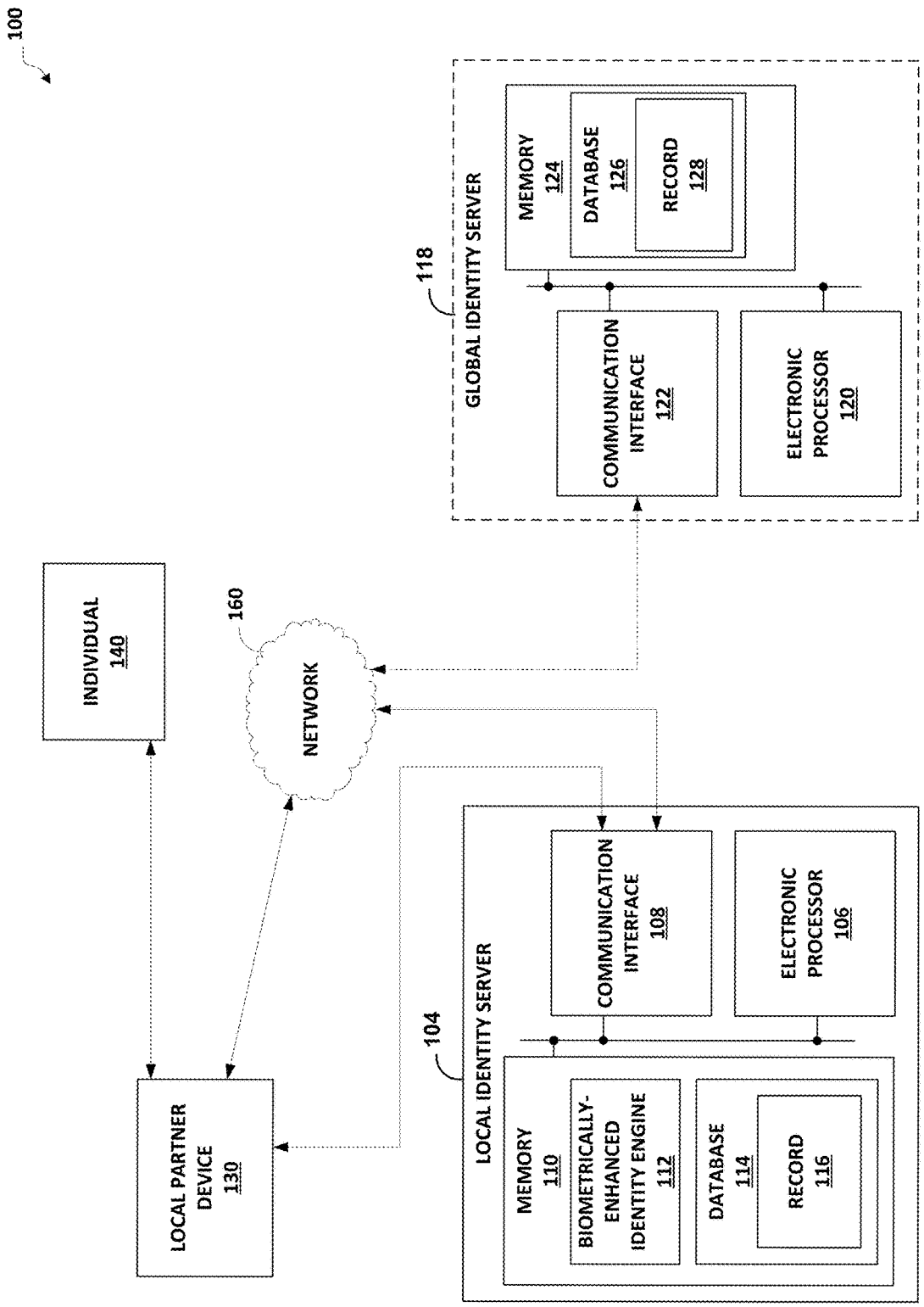
FIG. 1 is a block diagram illustrating an example system 100 for securely identifying and verifying an individual in a biometrically-enhanced data exchange or data storage.

FIG. 1 is a block diagram illustrating an example system 100 for securely identifying and verifying an individual in a biometrically-enhanced data exchange or data storage, in accordance with various aspects of the present disclosure. In the example of FIG. 1, the system 100 includes a local identity server 104, an optional global identity server 118, a local partner device 130, an individual 140, and a network 160.

The local identity server 104 and the optional global identity server 118 may be owned by, or operated by or on behalf of, an administrator. The optional global identity server 118 may also be implemented by one or more networked computer servers.

The local identity server 104 includes an electronic processor 106, a communication interface 108, and a memory 110. The electronic processor 106 is communicatively coupled to the communication interface 108 and the memory 110. The electronic processor 106 is a microprocessor or another suitable processing device. The communication interface 108 may be implemented as one or both of a wired network interface and a wireless network interface. The memory 110 is one or more of volatile memory (e.g., RAM) and non-volatile memory (e.g., ROM, FLASH, magnetic media, optical media, et cetera). In some examples, the memory 110 is also a non-transitory computer-readable medium. Although shown within the local identity server 104, memory 110 may be, at least in part, implemented as network storage that is external to the local identity server 104 and accessed via the communication interface 108. For example, all or part of memory 110 may be housed on the "cloud."

The optional global identity server 118 includes an electronic processor 120, a communication interface 122, and a memory 124. The electronic processor 120 is communicatively coupled to the communication interface 122 and the memory 124. The electronic processor 120 is a microprocessor or another suitable processing device. The communication interface 122 may be implemented as one or both of a wired network interface and a wireless network interface. The memory 124 is one or more of volatile memory (e.g., RAM) and non-volatile memory (e.g., ROM, FLASH, magnetic media, optical media, et cetera). In some examples, the memory 124 is also a non-transitory computer-readable medium. The memory 124 may be, at least in part, implemented as network storage that is external to the optional global identity server 118 and accessed via the communication interface 122. For example, all or part of memory 124 may be housed on the "cloud." Additionally, some or all of the functions attributed to the local identity server 104 may also be performed by the optional global identity server 118.

The biometrically-enhanced identity engine 112 may be stored within a transitory or non-transitory portion of the memory 110. The biometrically-enhanced identity engine 112 includes machine readable instructions that are executed by the electronic processor 106 to perform the functionality of the local identity server 104 as described below with respect to FIGS. 2-21.

The memory 110 may include a database 114 for storing information about individuals. The database 114 may be an RDF database, i.e., employ the Resource Description Framework. Alternatively, the database 114 may be another suitable database with features similar to the features of the Resource Description Framework, and various non-SQL databases, knowledge graphs, etc. The database 114 may include a plurality of records (also referred to herein as a "data pod"). Each record may be associated with and contain personal information about one individual. For example, in the illustrated embodiment, record 116 may be associated with the individual 140, and other N records may be respectively associated with one of N other individuals (not expressly shown in FIG. 1).

The local partner device 130 may be web-compatible mobile computer, such as a laptop, a tablet, a smart phone, or other suitable computing device. Alternately, or in addition, the local partner device 130 may be a desktop computer. The local partner device 130 includes an electronic processor in communication with memory. In an embodiment, the electronic processor of the computer 130 is also in communication with a biometric scanner via a communication interface. In another embodiment, the biometric scanner may be part of the local partner device 130. The electronic processor is a microprocessor or another suitable processing device, the memory is one or more of volatile memory and non-volatile memory, and the biometric scanner is one or more biometric scanning devices (e.g., a device that scans fingerprints, facial features, irises, handwriting, etc.) now known or subsequently developed. The communication interface may be a wireless or wired network interface.

An application, which contains software instructions implemented by the electronic processor of local partner device 130 to perform the functions of the local partner device 130 as described herein, is stored within a transitory or a non-transitory portion of the memory. The application may have a graphical user interface that facilitates interaction between the individual 140 and the local identity server 104.

The local partner device 130 may include or be in communication with a point of sale system (POS), e.g., a mobile POS system (such as a mobile card reader). As discussed herein, the local partner device 130 may use the mobile POS system to, among other things, read a partner-specific identification asset (not shown and considered to be part of the block "individual 140") associated with the individual 140 to verify the identity of the individual 140.

The local partner device 130 may communicate with the local identity server 104 over the network 160. The network 160 is preferably (but not necessarily) a wireless network, such as a wireless personal area network, local area network, or other suitable network. The local partner device 130 may directly communicate with the local identity server 104 or indirectly communicate over network 160.

In an embodiment, the memory of the local partner device 130 may include a database and software. The database of the local partner device 130 may include information about individual 140 and other individuals, as set forth herein. The software of the local partner device 130 may facilitate interaction between the local partner device 130 and individuals (e.g., the individual 140) and allow for the local partner device 130 to track the interactions as described in greater detail below.

The local identity server 104 may likewise communicate with partner devices other than the local partner device 130. The term "partner", as used herein, encompasses any other organizations engaging with individuals, including but not limited to non-governmental organizations and other charitable institutions (including governmental organizations). The term "individual", as used herein, encompasses a person (or household) that seeks to interact with an organization or entity, including but not limited to seeking access to services (e.g., an individual in a refugee camp, a person who receives support, etc.). The workings of the local identity server 104 and the local partner device 130 will now be described in additional detail with FIGS. 2-21.

Figure 2:
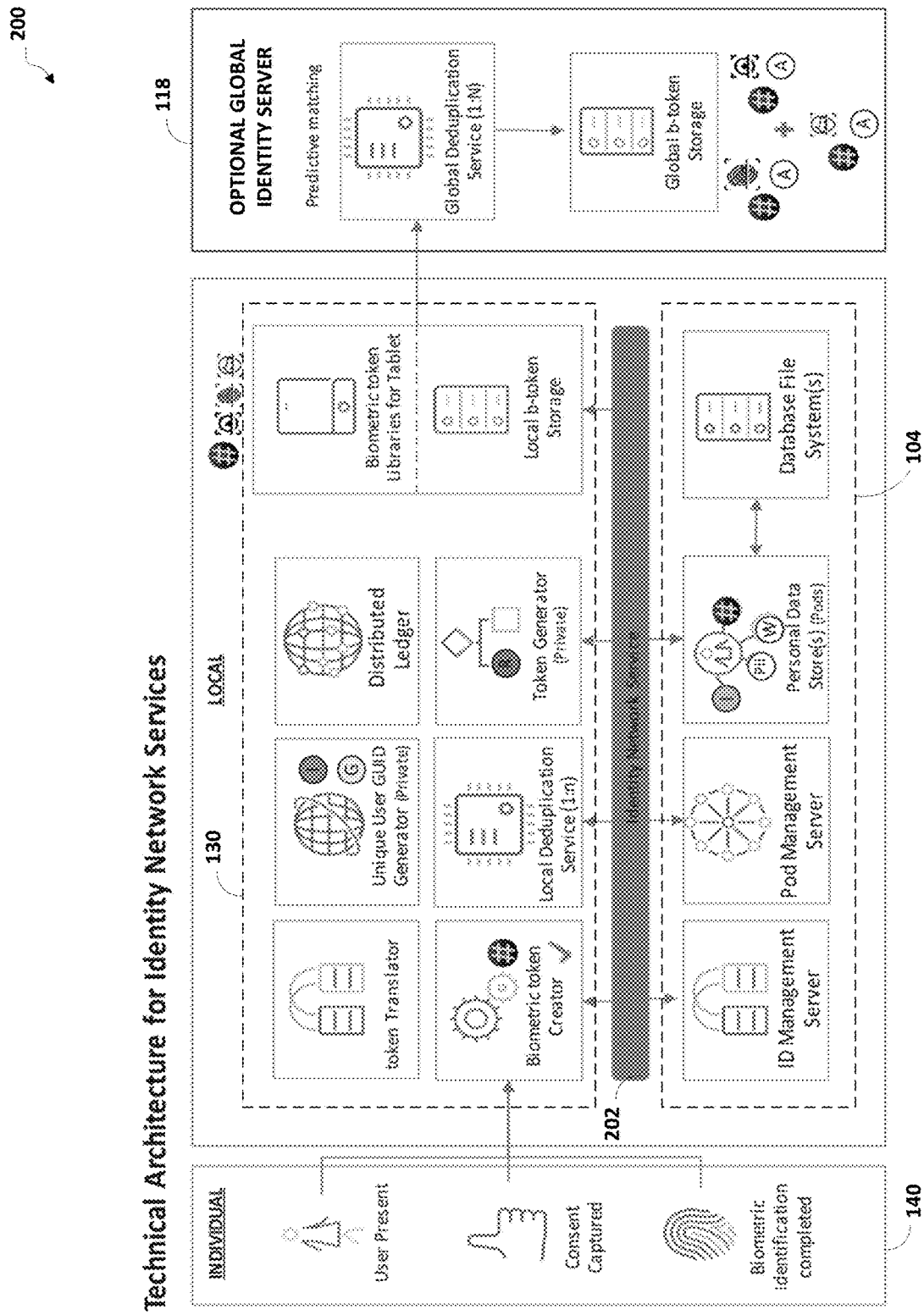
FIG. 2 is a block diagram illustrating a more detailed example of the system of FIG. 1 for securely identifying an individual.

FIG. 2 is a block diagram illustrating a more detailed example 200 of the system 100 for securely identifying an individual, in accordance with various aspects of the present disclosure. In the example of FIG. 2, the example 200 includes an identity (ID) network/switch 202 that connects a local partner device 130 to the local identity server 104. The local partner device 130 is also connected to the optional global identity server 118.

The local partner device 130 includes an electronic processor and a memory. The memory includes a token translator 204, a unique user global unique identifier (GUID) generator 206, a distributed ledger 208, a biometric token creator 210, a local deduplication service 212, a token generator 214, biometric token libraries 216, and a local b-token storage 218.

The local identity server 104 includes an identity management service 220, a pod management service 222, a plurality of personal data stores 224 (also referred to as "data pods"), and a database file system 226.

The optional global identity server 118 includes an electronic processor and a memory. The memory includes a global deduplication service 228 and a global biometric token storage 230.

In the example of FIG. 2, the individual 140 consents to biometric capture by the local partner device 130. The local partner device 130 create a biometric token from the biometric capture of the individual 140 with the biometric token creator 210. The biometric token creator 210 creates a biometric token with a tokenization algorithm.

Figure 3:
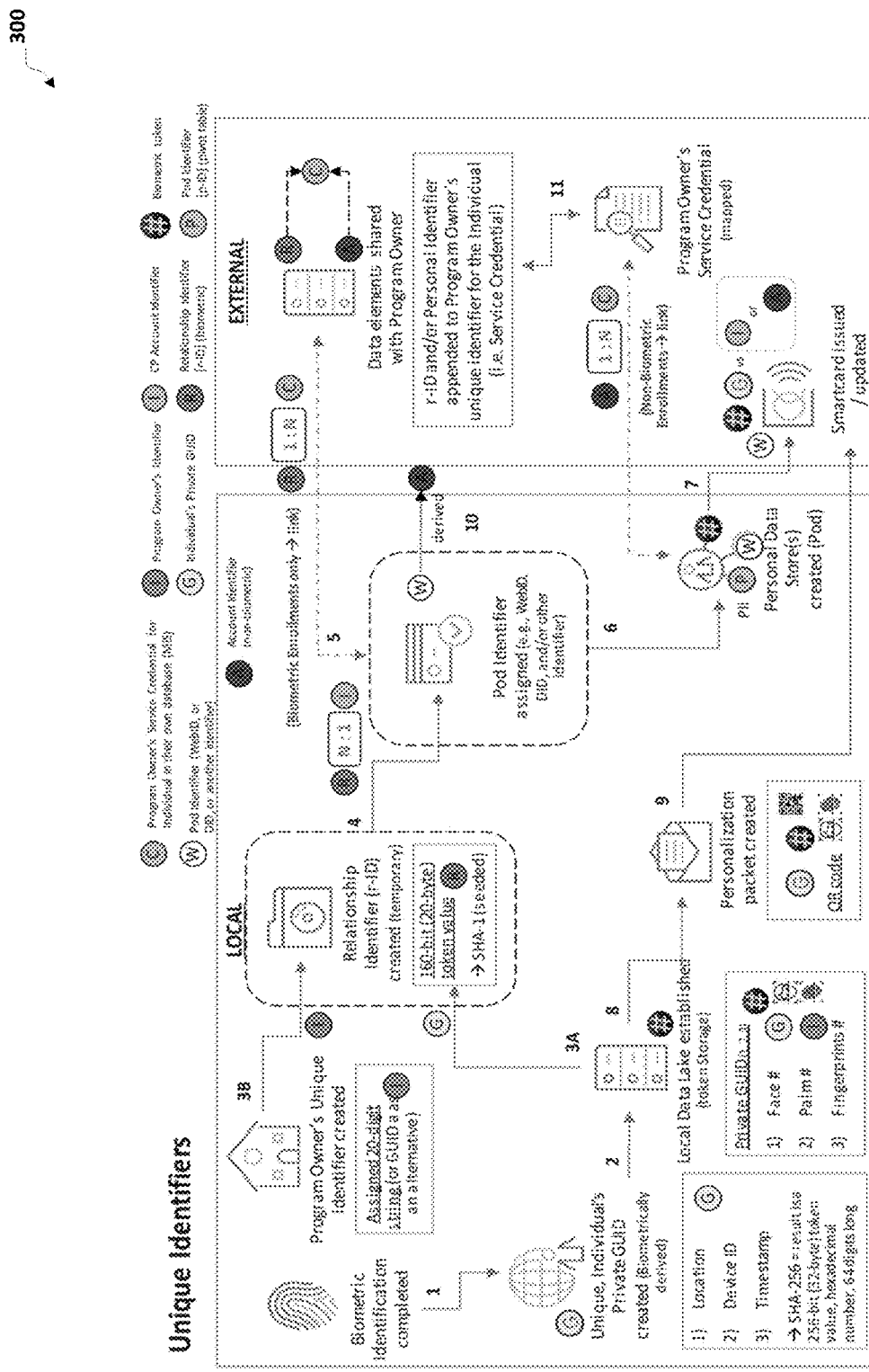
FIG. 3 is a flow diagram illustrating an example operation of the system of FIG. 1 for registering/enrolling the individual in an identity network services platform.

FIG. 3 is a flow diagram illustrating an example operation 300 of the system 100 of FIG. 1 for registering/enrolling the individual 140 in an identity network services platform, in accordance to various aspects of the present disclosure. In the example of FIG. 3, after capturing the biometrics of the individual 140 (at link 1), the local partner device 130 creates a unique and private global universal identifier (GUID) token with the unique GUID generator 206 (at link 2). In some examples, the unique and private GUID token is biometrically-derived from the captured biometrics. In other examples, the unique and private GUID token is not biometrically-derived. For example, the unique and private GUID token may simply be a random number.

Additionally, the local partner device 130 generates a biometric token from the captured biometrics and stores the biometric token in the local b-token storage 216 (at link 3A). The local partner device 130, in parallel to creating and storing the biometric token, also retrieves an assigned unique identifier that is associated with the owner of the local partner device 130 (at link 3B). The local partner device 130 receives the unique and private GUID token and creates, with the token generator 214, a relationship identifier token from the unique identifier associated with the owner and the unique and private GUID token (at links 3A and 3B).

In some examples, the local partner device 130 generates a high-level identifier "W" token from the relationship identifier token (at link 4). The high-level identifier "W" token is a pod identifier (e.g., WebID, DID, or another unique identifier) assigned to a new data pod. In other examples, the local partner device 130 may use the relationship identifier or the biometric token instead of the high-level identifier.

The local partner device 130 assigns a first pod identifier token, e.g., a webID, DID, or another unique identifier (at link 6). After assigning the pod identifier, the local partner device 130 creates a personal data store (also referred to as a "pod" or "data pod") by creating a second pod identifier token (i.e., a p-ID) that is tied to a pivot table (at link 7). The pivot table stores various information in the pod, e.g., the biometric token, the first pod identifier token, the second pod identifier token, and/or other suitable information.

In parallel to links 3A-7, the local partner device 130 receives the biometric token, the GUID token, and information regarding the type of biometric capture from the local partner device 130 (at link 8). In response to receiving the biometric token, the GUID token, and the information regarding the type of biometric capture, the local partner device 130 creates a personalized packet and a QR code. After creating the personalized packet, the local partner device 130 issues a smartcard or other identification vehicle that includes the high-level identifier, the biometric token, the unique and private GUID token (at links 9 and 10).

Lastly, FIG. 3 is described with respect to the local partner device 130. However, FIG. 3 is limited to being performed by the local partner device 130. Instead, FIG. 3 may also be performed at least in part by the local identity server 104. For example, after receiving the biometrics of the individual 140 that are captured, the local identity server 104 may perform all of the functions described above with respect to the local partner device 130.

In a different example, the local identity server 104 may receive the high-level identifier, the biometric token, the unique and private GUID token, and the local identity server 104 creates a personalized packet and a QR code. After creating the personalized packet, the local identity server 104 issues a smartcard or other identification vehicle that includes the high-level identifier, the biometric token, the unique and private GUID token (at links 9 and 10).

Figure 4:
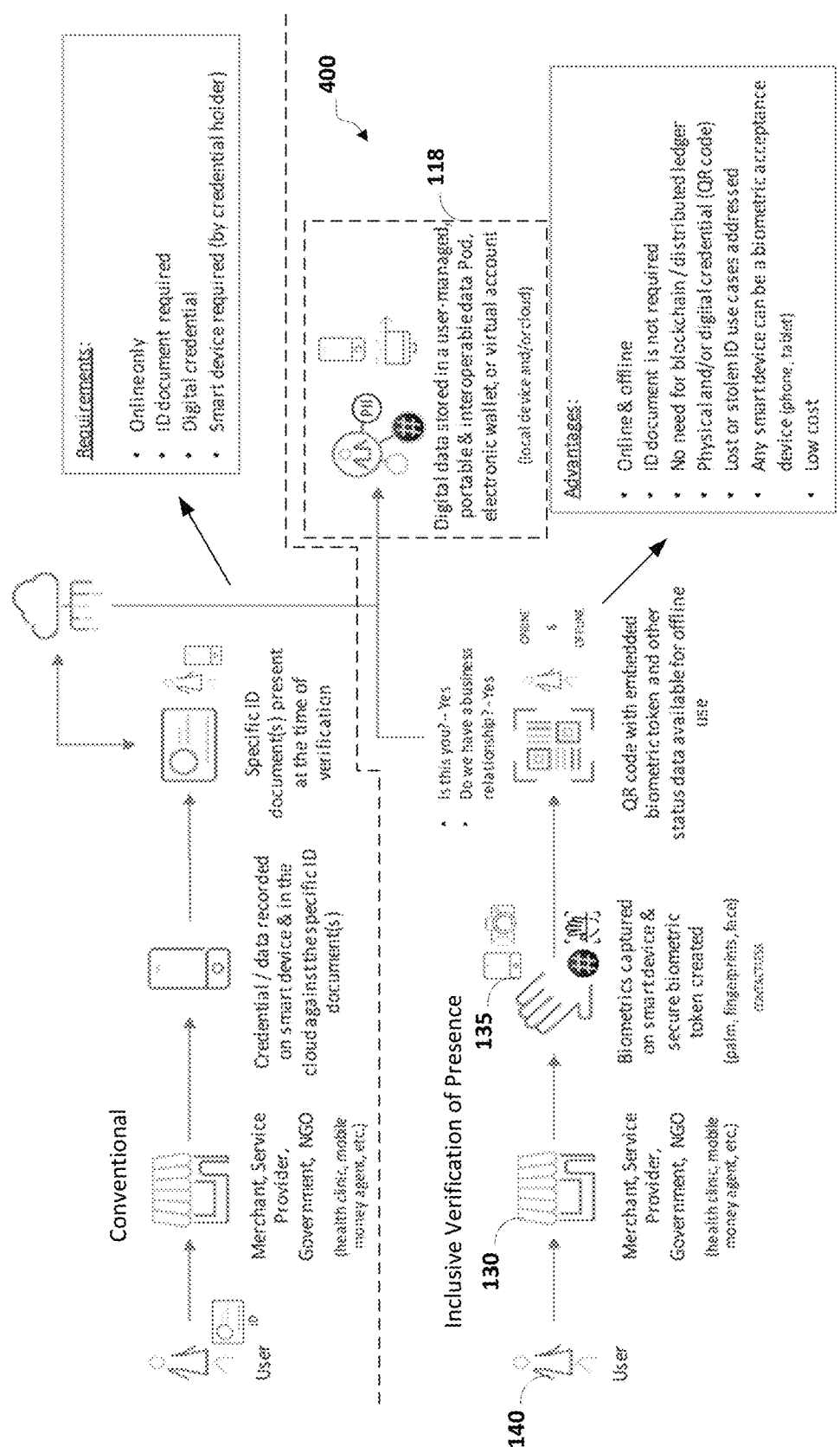
FIG. 4 is a diagram illustrating a comparison between conventional verification of presence and inclusive verification of presence.

FIG. 4 is a diagram illustrating a comparison between conventional verification of presence and inclusive verification of presence 400, in accordance with various aspects of the present disclosure. Conventionally, as illustrated in FIG. 4, a user takes a user identification (ID) card to a merchant, service provider, government, or non-governmental organization. A digital credential and/or data is recorded on a user's smart device and in the cloud against the specific user ID card. Lastly, specific identification documents must be present at the time of verification. Thus, the conventional verification of presence requires an online connection, an identification document, a digital credential, and the user's smart device.

With respect to the inclusive verification of presence 400, the user 140 may go to a merchant, service provider, government, or non-governmental organization without a user ID card and without a user's smart device. The merchant, service provider, government, or non-governmental organization uses a biometric capture device to capture biometrics of the user 140. A secure biometric token is created by the biometric capture device or other smart device with a biometric token generation application that receives biometrics from the biometric capture device.

In the inclusive verification of presence 400, the biometric capture device or other smart device may generate a QR code with an embedded form of the secure biometric token that is created. The QR code may also include other status data available for offline use.

Additionally, the biometric capture device or other smart device may send the secure biometric token to a user-managed, portable, and interoperable data pod, electronic wallet, or virtual account. In other words, the biometric capture device or other smart device makes the secure biometric token available both locally and globally.

The inclusive verification of presence 400 has several advantages over the conventional verification of presence. First, the inclusive verification of presence 400 is available both online and offline. Second, the inclusive verification of presence 400 does not require any identification documents. Third, the inclusive verification of presence 400 does not require any blockchain or distributed ledger. Fourth, the inclusive verification of presence 400 is not affected by lost or stolen identification documents. Fifth, the biometric capture device at the merchant, service provider, government, or non-governmental organization may be any biometric acceptance device (e.g., smartphones, tablets, or other suitable biometric acceptance devices).

The advantages of the inclusive verification of presence 400 is from biometric tokenization. By capturing biometrics and embedding biometric tokens (associated with the buyer, i.e., the individual 140) in a QR code, which may be put on the card itself and linked with the prepaid card details (on QR code, and on the issuer's backend). The biometric tokens may also be issued via some other digital means and linked to the specific, issued prepaid card.

The individual 140 may verify ownership of the prepaid card against the QR code on the card. Additionally, the QR code lists last four digits of the prepaid card to show it is "linked" to that card, although any means to link the QR code to the prepaid card may be used.

The individual 140 may also regain the prepaid card balance the prepaid card is lost or stolen because the individual 140 may demonstrate ownership of that prepaid card. Moreover, the prepaid card issuer is able to store or access the link between biometric token and prepaid card.

Figure 5:
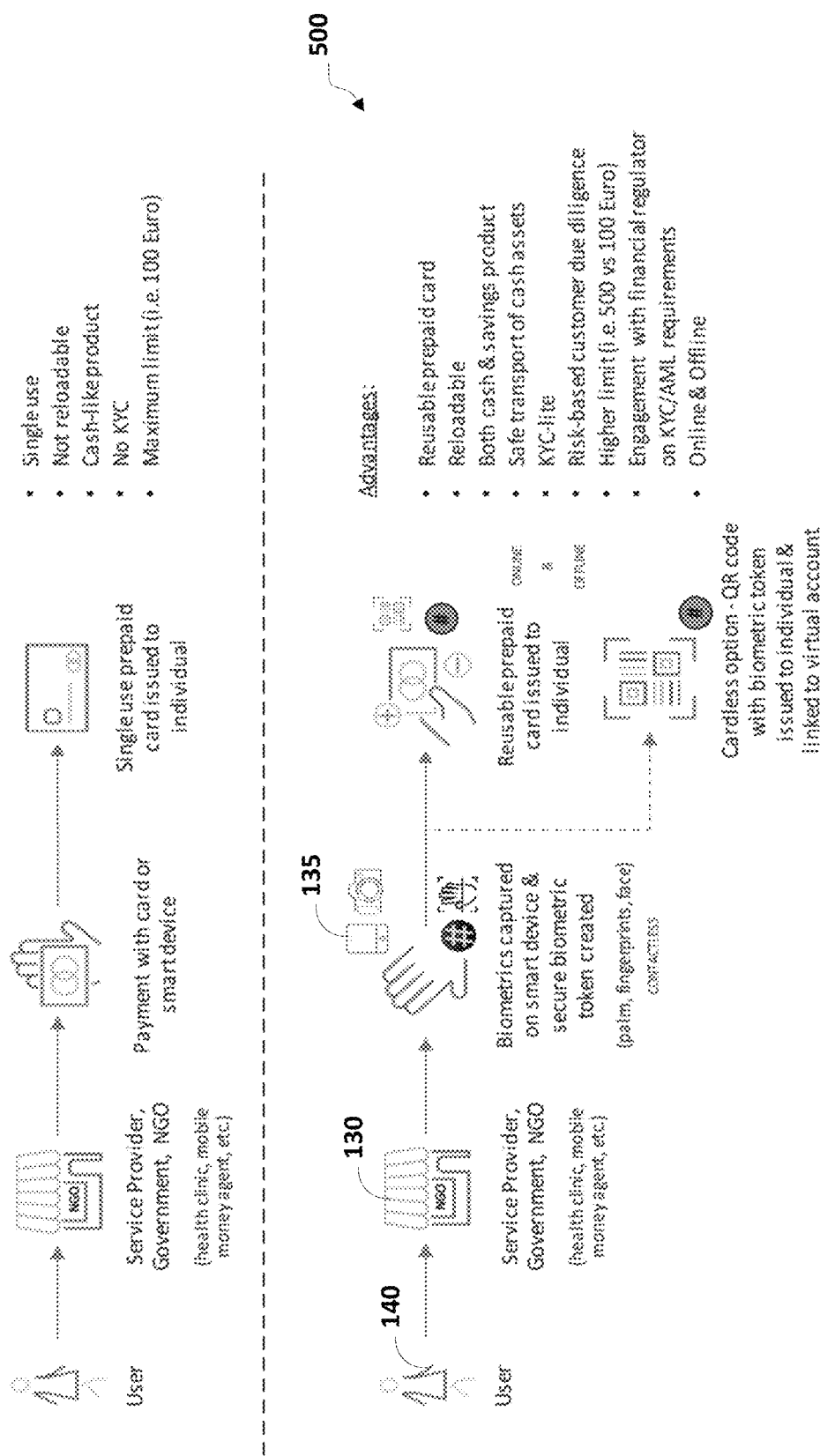
FIG. 5 is a diagram illustrating a comparison between conventional verification of presence with a financial product and inclusive verification of presence with a financial product.

FIG. 5 is a diagram illustrating a comparison between conventional verification of presence with a financial product and inclusive verification of presence 500 with a financial product, in accordance with various aspects of the present disclosure. Conventionally, as illustrated in FIG. 5, a user takes a payment card or payment device to a merchant, service provider, government, or non-governmental organization. A payment is made with the payment card or the payment device and a single use prepaid card is issued to the individual. Thus, the conventional verification of presence requires an online connection, an identification document, a digital credential, and the user's smart device.

With respect to the inclusive verification of presence 500, the user 140 may go to a merchant, service provider, government, or non-governmental organization without a payment card or a payment device. The merchant, service provider, government, or non-governmental organization uses a biometric capture device to capture biometrics of the user 140. A secure biometric token is created by the biometric capture device or other smart device with a biometric token generation application that receives biometrics from the biometric capture device.

In the inclusive verification of presence 500, the biometric capture device or other smart device may generate a QR code with an embedded form of the secure biometric token that is created. The QR code may also include virtual payment account information that is available for both online and offline use.

Additionally, the biometric capture device or other smart device may be embedded into a reusable prepaid card issued to the individual 140. In other words, the biometric capture device or other smart device makes a virtual account or a reusable prepaid card available and verifiable online and offline.

The inclusive verification of presence 500 has several advantages over the conventional verification of presence. First, the inclusive verification of presence 500 is available both online and offline. Second, the inclusive verification of presence 500 does not require any identification documents. Third, the inclusive verification of presence 500 does not require any blockchain or distributed ledger. Fourth, the inclusive verification of presence 500 is not affected by lost or stolen reusable prepaid cards. Fifth, the biometric capture device at the merchant, service provider, government, or non-governmental organization may be any biometric acceptance device (e.g., smartphones, tablets, or other suitable biometric acceptance devices). Sixth, the prepaid card is reloadable and reusable and meets some know-your-customer (KYC) requirements.

Figure 6:
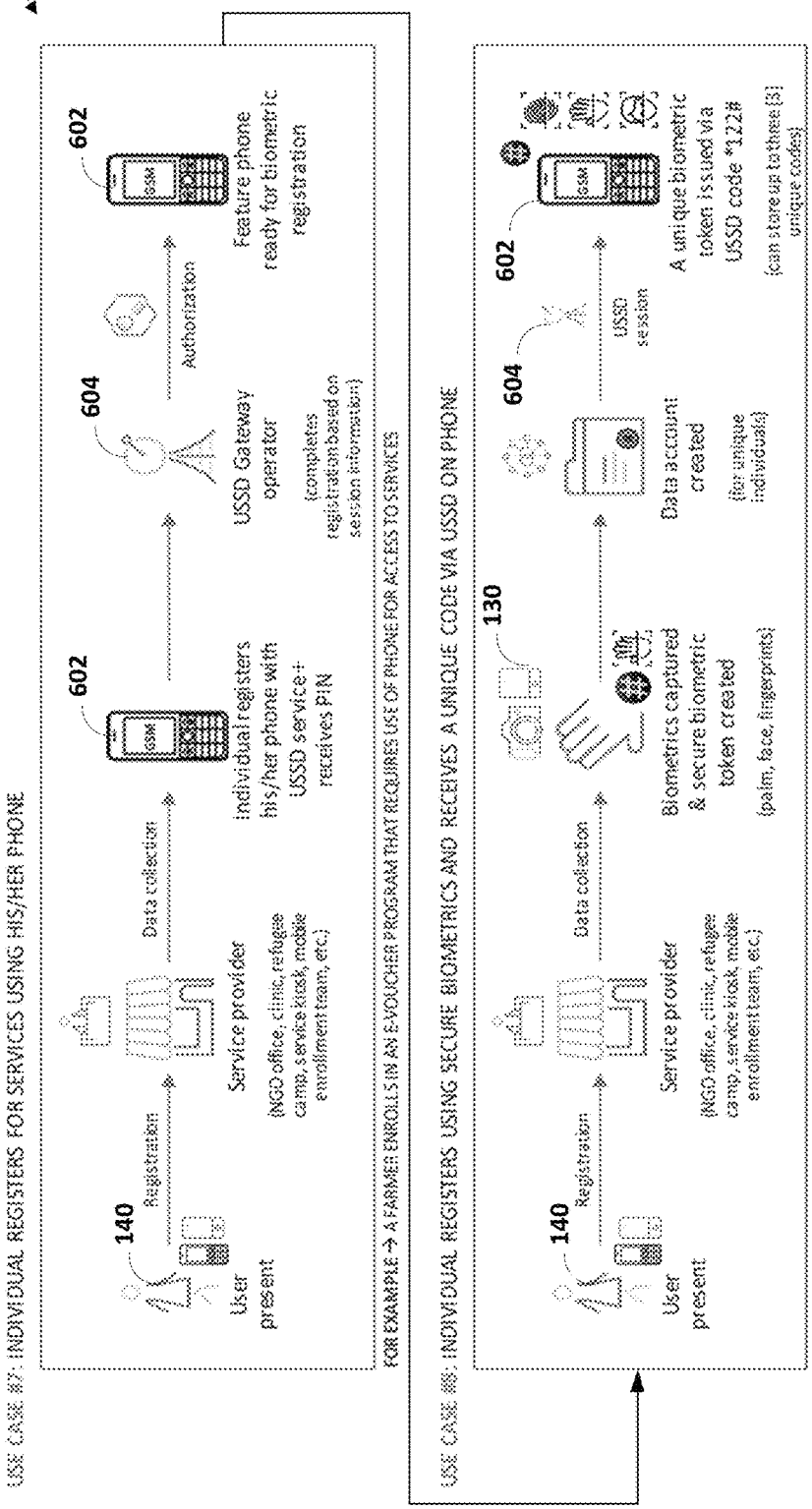
FIG. 6 is a flow diagram illustrating an example for issuing a digital identity credential of a registered individual with the system of FIG. 1.

FIG. 6 is a flow diagram illustrating an example 600 for issuing a digital identity credential of a registered individual with the system 100 of FIG. 1, in accordance to various aspects of the present disclosure. In example 600 of FIG. 6, the individual 140 registers a computing device 602 (e.g., a computing device as illustrated in FIG. 6) with a service provider. The service provider is an owner of the local partner device 130 as described above in FIG. 1.

The individual 140 receives a PIN and completes registration of the computing device 602 with a USSD Gateway operator 604 based on session information. The completed registration with the USSD Gateway operator 604 authorizes the computing device 602 to receive biometric registration. In some examples, operators other than the USSD Gateway operator 604 may be used.

The individual 140 then presents the registered computing device 602 to the service provider. The service provider captures biometrics of the individual 140 with the local partner device 130 as described above in FIG. 1.

In response to capturing the biometrics of the individual 140, the local partner device 130 creates a unique data account (e.g., a data pod as described above in FIG. 3). Additionally, in response to capturing the biometrics of the individual, the local partner device 130 generates a biometric token, associates the biometric token with the unique data account, and issues the biometric token as a USSD code via a USSD session. For example, the USSD code may be *122#.

In some examples, the example 600 may be a farmer enrolling in an e-voucher program that requires use of a phone for access to services. The farmer receives a unique code based on the farmer's biometrics on the phone for future verifications.

Additionally, in some examples, the biometric token may be too large to store on a feature phone via a USSD menu. In these examples, a web link or a pointer to the place where the biometric token is stored may be used instead of the biometric token via the USSD menu. The web link or a pointer may be facilitated with a mobile wallet and the USSD menu. Specifically, the individual 140 may have his/her biometric tokens captured and stored in a location that is shared with the individual 140 via the USSD menu and the mobile wallet access, and perhaps link to other data about the individual 140. In these examples, once the individual 140 successfully verifies against the stored biometric token "living" behind a web link/pointer, only then will other personal data associated with the individual 140 will be shared or released.

Figure 7:
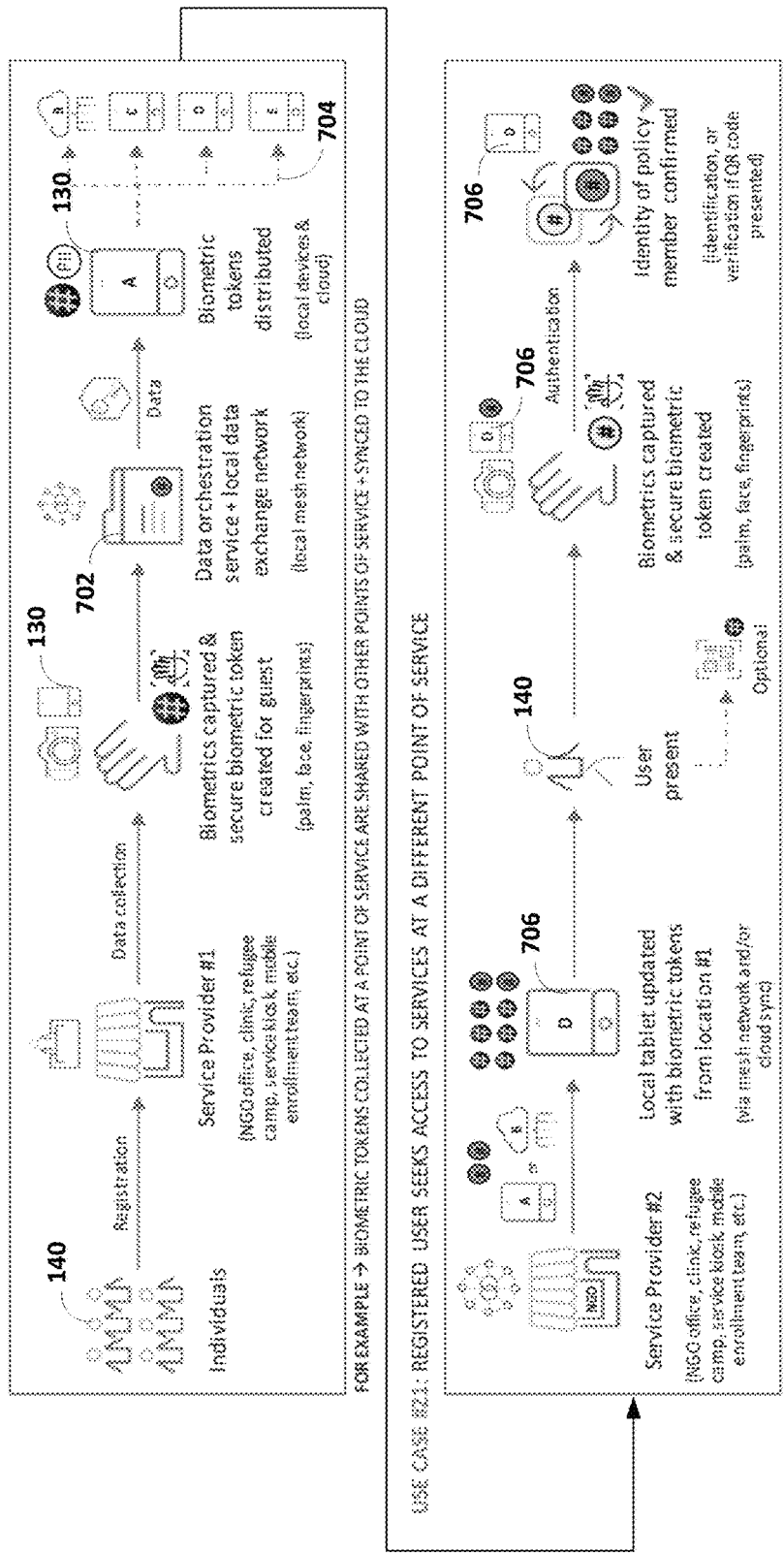
FIG. 7 is flow diagram illustrating example for registering and accessing decentralized points of service with the system of FIG. 1.

FIG. 7 is flow diagram illustrating example 700 for registering and accessing decentralized points of service with the system 100 of FIG. 1, in accordance to various aspects of the present disclosure.

In example 700 of FIG. 7, the individual 140 registers with a service provider by providing biometrics to the service provider. The service provider captures the biometrics of the individual 140 with the local partner device 130 as described above in FIG. 1. The local partner device 130 generates a biometric token based on the captured biometrics.

In response to generating the biometric token, the local partner device 130 executes a data orchestration service 702 to distribute the biometric token to the cloud and one or more local devices via a local data exchange network 704. The one or more local devices are additional decentralized points of service.

In the example 700 of FIG. 7, a second local partner device 706 (similar to the local partner device 130 of FIG. 1) associated with a second service provider receives the biometric token either locally from the local partner device 130 or from the cloud via the local data exchange network 704. The second local partner device 706 updates the b-token storage to include the biometric token from the local partner device 130.

In the example 700 of FIG. 7, the individual 140 accesses services from the second service provider by providing biometrics to the second service provider. The second service provider captures the biometrics of the individual 140 with the second local partner device 706. The second local partner device 706 generates a second biometric token based on the captured biometrics. In some examples, the biometrics provided to the second service provider is a QR code generated by the local partner device 130 and indicative of the distributed biometric token.

In response to generating the second biometric token, the second local partner device 706 compares the second biometric token to tokens stored in the local b-token storage. The second local partner device 706 confirms an identity of the policy member when the second biometric token substantially matches the biometric token that was distributed and stored in the local b-token storage.

In the example of FIG. 7, rather than storing biometric tokens centrally, in the cloud, the local partner device 130 or the local identity server 104 may distribute biometric tokens to mobile devices or keep the biometric tokens created on that mobile device, instead of just sending that data to the cloud. In other words, the local partner device 130 or the local identity server 104 may create a distributed version of the central cloud-based biometric token vault.

Additionally, in some cases, the distribution of personal data is unnecessary and only a biometric token is necessary. For example, the biometric token may represent "membership" in a particular program or association with a particular entity, so that any person matching that biometric token is the individual 140 and allowed to receive certain benefits based on the relationship between the individual and the particular program or the particular entity.

Further, in some examples, the registration process of FIG. 7 includes pre-registration for individuals that do not have all documents at the time of registration with a particular entity (for example, banks in rural areas via traveling registration vehicles). The particular entity may, with the local partner device 130 (e.g., a mobile device or a registration terminal), register the person, collect other relevant data, and bind the entire application to one or more biometric token(s) when identity (ID) documents are insufficient. When the pre-registration is in complete, the individuals may continue the application in the future when the same person (matching the biometric tokens) shows up at the particular entity to continue the registration process.

Furthermore, in some examples, the registration process of FIG. 7 may involve a plurality of local partner devices including the local partner device 130. In these examples, the plurality of local partner devices may sync biometric tokens with each other when online or communicatively connected to each other. The syncing of biometric tokens with each other reduces or eliminates a possibility of registering the individual 140 more than once even when the local partner device 130 is offline. In some examples, the plurality of local partner device may sync by proximity using Bluetooth®, a physical cable, Wi-Fi, or other suitable communication means.

Figure 8:
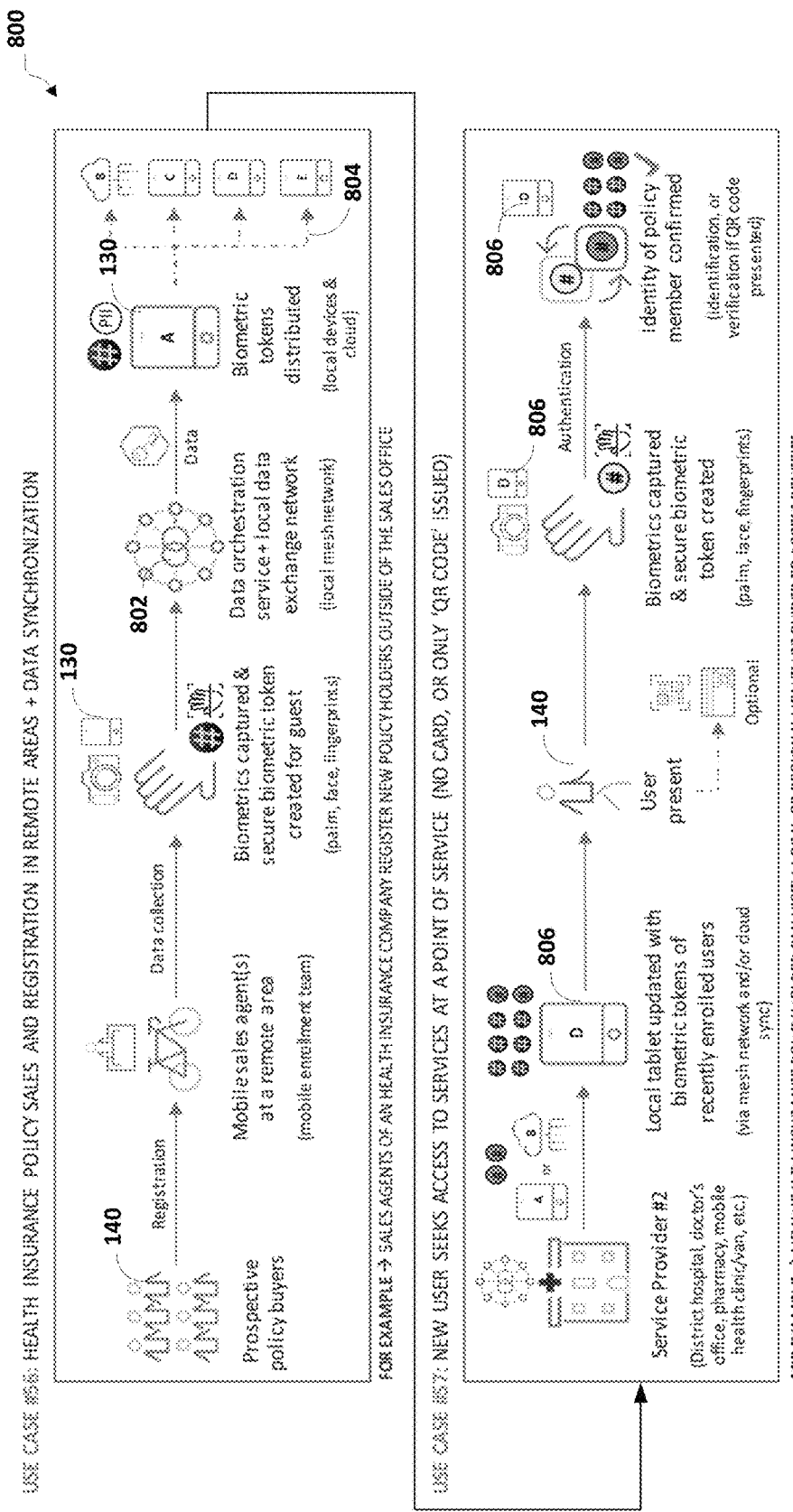
FIG. 8 is flow diagram illustrating example for registering and accessing healthcare with the system of FIG. 1.

FIG. 8 is flow diagram illustrating example 800 for registering and accessing healthcare with the system 100 of FIG. 1, in accordance to various aspects of the present disclosure.

In example 800 of FIG. 8, the individual 140 purchases health insurance from a health insurance provider by providing biometrics to an agent of the health insurance provider. The agent captures the biometrics of the individual 140 with the local partner device 130 as described above in FIG. 1. The local partner device 130 generates a biometric token based on the captured biometrics.

In response to generating the biometric token, the local partner device 130 executes a data orchestration service 802 to distribute the biometric token to the cloud and one or more local devices via a local data exchange network 804. The one or more local devices are computing devices located at various healthcare facilities that are associated with the health insurance provider.

In the example 800 of FIG. 8, a second local partner device 806 (similar to the local partner device 130 of FIG. 1) associated with one of the healthcare facilities receives the biometric token either locally from the local partner device 130 or from the cloud via the local data exchange network 804. The second local partner device 806 updates the b-token storage to include the biometric token from the local partner device 130.

In the example 800 of FIG. 8, the individual 140 accesses services from the one of the healthcare facilities by providing biometrics to the healthcare facility. The healthcare facility captures the biometrics of the individual 140 with the second local partner device 806. The second local partner device 806 generates a second biometric token based on the captured biometrics. In some examples, the biometrics provided to the healthcare facility is a QR code generated by the local partner device 130 and indicative of the distributed biometric token.

In response to generating the second biometric token, the second local partner device 806 compares the second biometric token to tokens stored in the local b-token storage. The second local partner device 806 confirms an identity of the policy member when the second biometric token substantially matches the biometric token that was distributed and stored in the local b-token storage.

Figure 9:
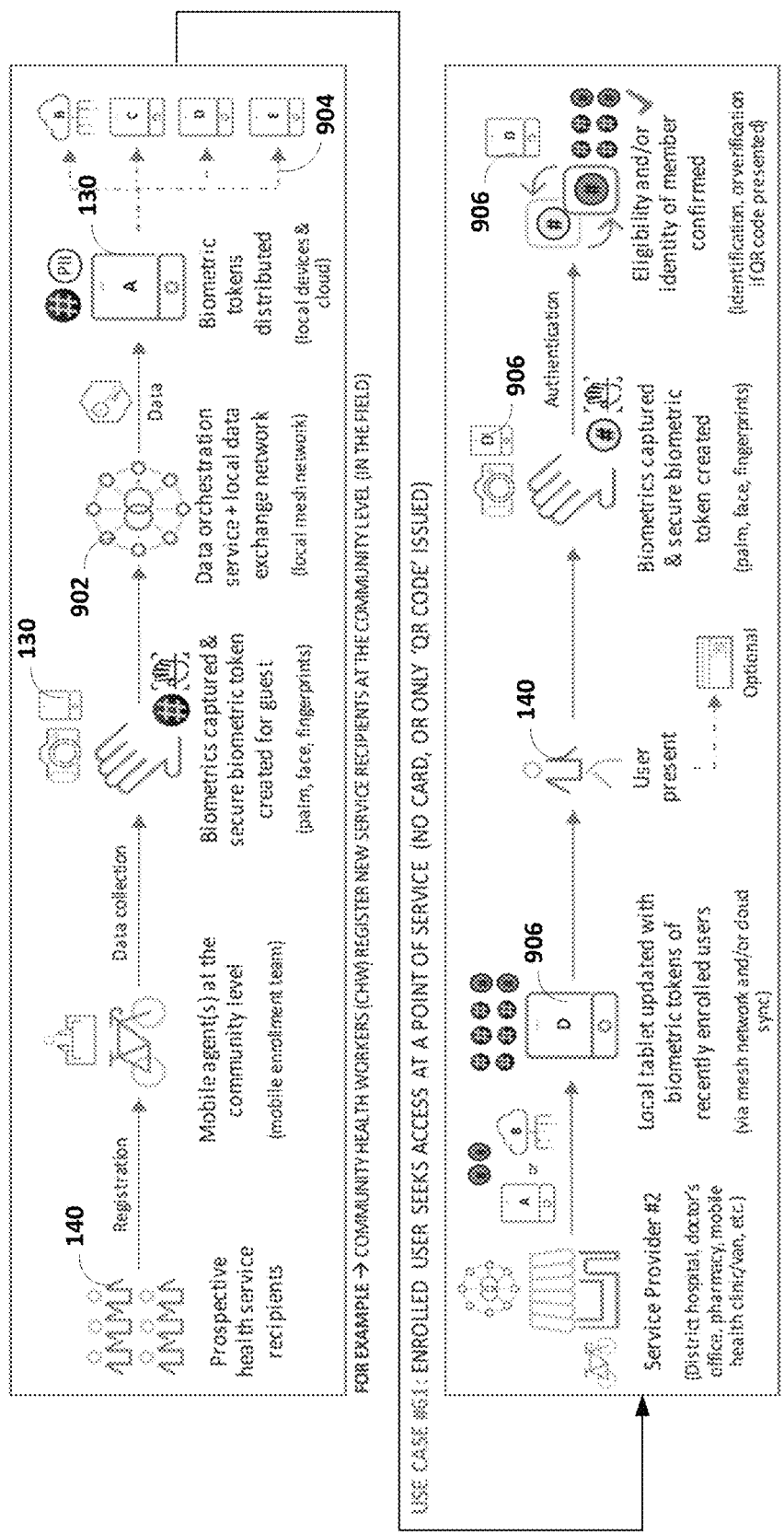
FIG. 9 is flow diagram illustrating example for registering for healthcare with the system of FIG. 1.

FIG. 9 is flow diagram illustrating example 900 for registering for healthcare with the system 100 of FIG. 1, in accordance to various aspects of the present disclosure.

In example 900 of FIG. 9, the individual 140 registers for health service by providing biometrics to an agent of a health service provider. The health service provider captures the biometrics of the individual 140 with the local partner device 130 as described above in FIG. 1. The local partner device 130 generates a biometric token based on the captured biometrics.

In response to generating the biometric token, the local partner device 130 executes a data orchestration service 902 to distribute the biometric token to the cloud and one or more local devices via a local data exchange network 904. The one or more local devices are computing devices located at various healthcare facilities that are associated with the health service provider.

In the example 900 of FIG. 9, a second local partner device 906 (similar to the local partner device 130 of FIG. 1) associated with one of the healthcare facility receives the biometric token either locally from the local partner device 130 or from the cloud via the local data exchange network 904. The second local partner device 906 updates the b-token storage to include the biometric token from the local partner device 130.

In the example 900 of FIG. 9, the individual 140 accesses services from the healthcare facility by providing biometrics to the healthcare facility. The healthcare facility captures the biometrics of the individual 140 with the second local partner device 906. The second local partner device 906 generates a second biometric token based on the captured biometrics. In some examples, the biometrics provided to the healthcare facility is a QR code generated by the local partner device 130 and indicative of the distributed biometric token.

In response to generating the second biometric token, the second local partner device 906 compares the second biometric token to tokens stored in the local b-token storage. The second local partner device 906 confirms an identity of the policy member when the second biometric token substantially matches the biometric token that was distributed and stored in the local b-token storage.

Figure 10:
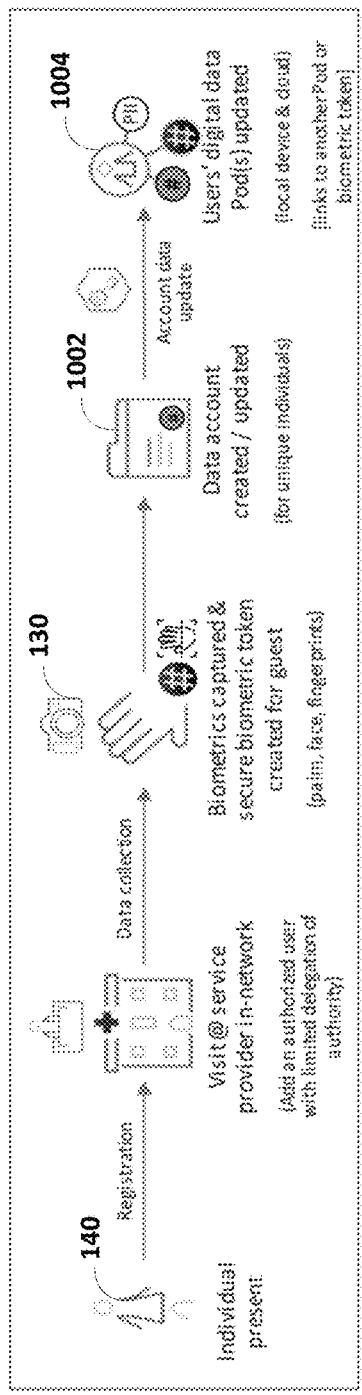
FIG. 10 is flow diagram illustrating examples for biometrically-enhancing data exchange and records matching with the system of FIG. 1.
Figure 10:
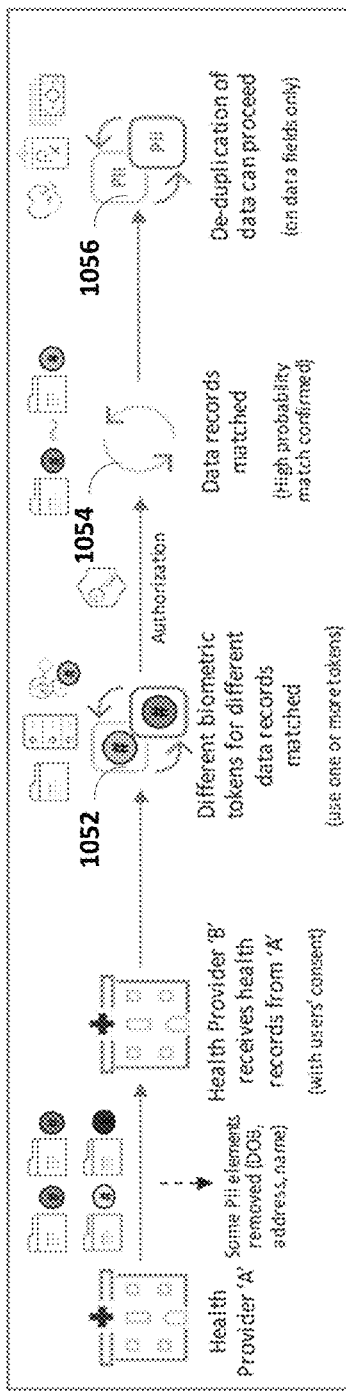

FIG. 10 is flow diagram illustrating examples 1000 and 1050 for biometrically-enhancing data exchange and records matching with the system 100 of FIG. 1, in accordance to various aspects of the present disclosure.

In example 1000 of FIG. 10, the individual 140 registers with a health service provider by providing biometrics to the health service provider. For example, the individual 140 adds an authorized user with limited delegation of authority.

The health service provider captures the biometrics of the individual 140 with the local partner device 130 as described above in FIG. 1. The local partner device 130 generates a biometric token based on the captured biometrics.

In response to generating the biometric token, the local partner device 130 creates or updates a data account 1002 that is unique to the individual. The local partner device 130 also updates a data pod 1004 associated with the individual 140 to include the biometric token and the authorized user information.

In the example 1050 of FIG. 10, with consent of the individual 140, a first health provider sends records to a second health provider. The records have some personally-identifiable information (PII) removed, e.g., date-of-birth, address, and name. However, the records each include a biometric token associated with the individual 140.

In response to receiving the records, the second health provider uses a second local partner device 1006 to match 1052 the biometric tokens in the records to one or more data pods or other records of the individual 140. The second local partner device 1006 then confirms a match 1054 when the match probability is a high probability (the high probability defined by industry standard or by service provider). Once a match has been confirmed, the second local partner device 1006 performs de-duplication 1056 of data between the matching records.

Matching of patient records using biometrics is a long-time 'dream' in healthcare industry but marred with challenges including some privacy risks. Moreover, biometric templates and biometric images are large, and considered very sensitive.

Conventionally, merging or sharing of medical records between two medical providers fails 50% of the time because of data errors, misspellings, missing data elements. Moreover, many medical providers do not use biometrics to match records because it presents some risks and both medical providers must use the same biometric vendor.

The examples 1000 and 1050 provide a number of distinct advantages. First, the size of the biometric tokens allows for embedding multiple biometric tokens into printed and digital medical records (for flexibility, as an as higher level of assurance). Second, the biometric tokens provide layered privacy because biometrics tokens of a face may be used for less sensitive records and biometric tokens of a palm may be embedded into more sensitive records, where you need my physical presence versus capturing my face on the street or using a facial photo. Third, even if data is wrong, missing, or misspelled, the biometric tokens in the records between different hospitals may still be matched with a "presence." Fourth, medical providers may provide medical help to individuals that intentionally or unintentionally give incorrect data and match them against other records for a more complete medical history. Fifth, medical provides may provide medical help to known individuals that are unconscious or unwilling to communicate and match them against other records for a more complete medical history. Sixth, appending biometric tokens to medical files/records is lower risk than biometric images/templates because biometric tokens may be revoked and are more secure than the biometric images/templates. Seventh, biometric matching may be used to fix data inaccuracy and/or misspellings for records with a very strong biometric match. Lastly, and most importantly, the choice of biometric vendor may be given to the individual 140 because the individual 140 may work with one partner to capture biometrics, generate tokens, and give the biometric tokens to each respective hospital for the purpose of appending to the medical record. Then, the individual 140 is at the center of the data exchange rather than the medical provider.

Figure 11:
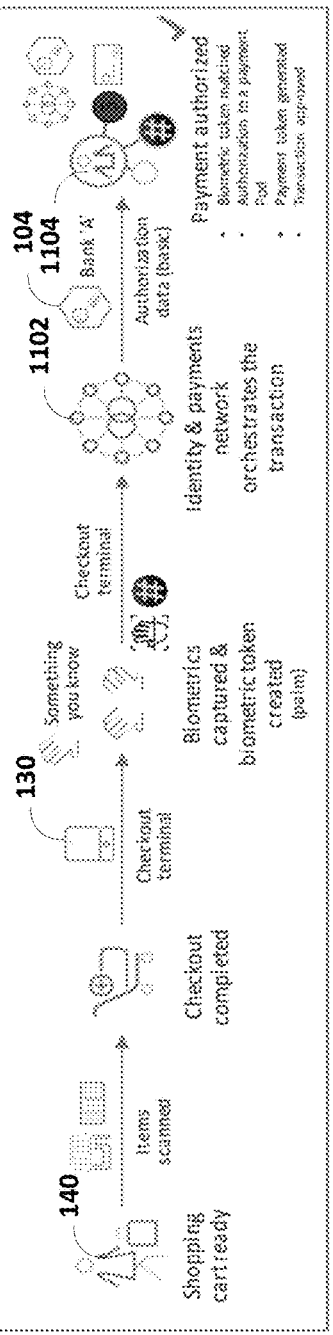
FIG. 11 is flow diagram illustrating examples for paying for items using biometrics versus smartphone with the system of FIG. 1.
Figure 11:
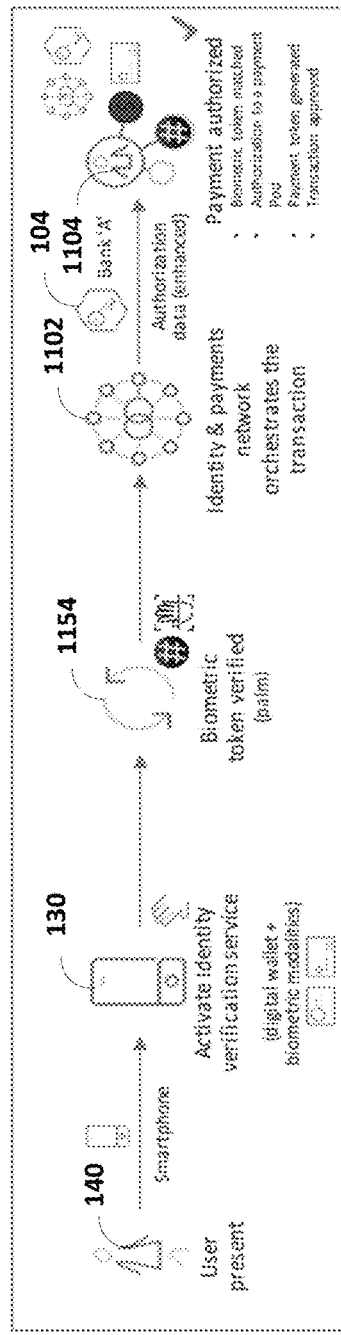

FIG. 11 is flow diagram illustrating examples 1100 and 1150 for paying for items using biometrics versus smartphone with the system 100 of FIG. 1, in accordance to various aspects of the present disclosure.

In example 1100 of FIG. 11, the individual 140 scans in items and completes checkout by providing biometrics to the local partner device 130 (e.g., a checkout terminal). The local partner device 130 captures the biometrics of the individual 140 and generates a biometric token based on the captured biometrics. In response to generating the biometric token, the local partner device 130 sends the biometric token to the local identity server 104 (e.g., a server administered by a bank) via an identity and payments network 1102.

The local identity server 104 matches the biometric token that is received from the local partner device 130 to a data pod 1104. The local identity server 104 confirms whether authorization to make a payment at the local partner device 130 exists in the data pod 1104. When the authorization exists, the local identity server 104 generates a payment token that approves the transaction at the local partner device 130 and sends the payment token to the local partner device 130 via the identity and payments network 1102.

In example 1150 of FIG. 11, the individual 140 scans in items and completes checkout by activating an identity verification service on the local partner device 130 (e.g., an identity verification service application on the individual's smartphone). The local partner device 130 includes a digital wallet and biometric modalities and requests a biometric capture of the individual 140.

The local partner device 130 captures the biometrics of the individual 140 and generates a biometric token based on the captured biometrics. The local partner device 130 verifies the biometric token that is generated matches a pre-existing token stored in the memory of the local partner device 130. In response to verifying the biometric token, the local partner device 130 sends the biometric token to the local identity server 104 (e.g., a server administered by a bank) via an identity and payments network 1102.

The local identity server 104 matches the biometric token that is received from the local partner device 130 to a data pod 1104. The local identity server 104 confirms whether authorization to make a payment at the local partner device 130 exists in the data pod 1104. When the authorization exists, the local identity server 104 generates a payment token that approves the transaction at the local partner device 130 and sends the payment token to the local partner device 130 via the identity and payments network 1102.

In summary of FIG. 11, biometric tokens may be created and embedded into a digital account (referred to herein as a "data pod") that belongs to the individual 140. The data pod includes payment tokens, identity data, and/or other data associated with the individual 140. Successful authentication into the data pod using one or more biometric token(s) may be used to unveil the link to payment information, to process the transaction.

Figure 12:
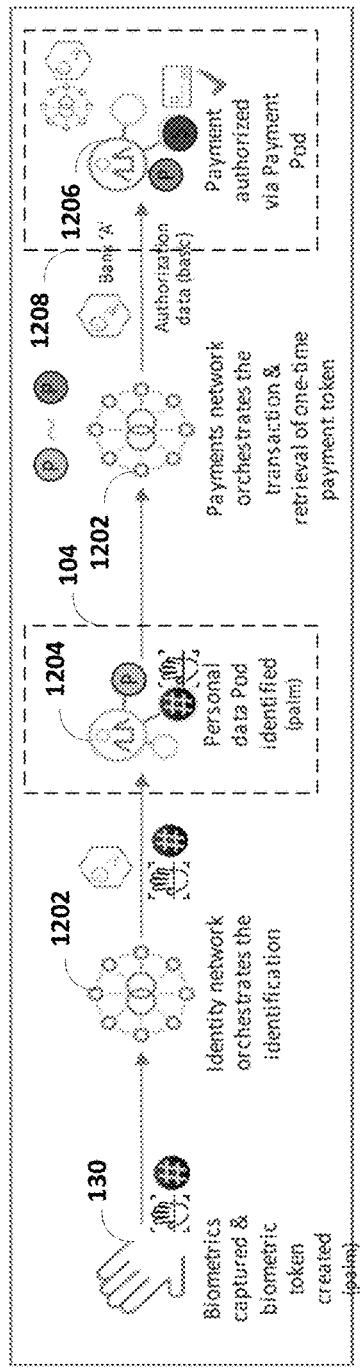
FIG. 12 is flow diagram illustrating examples for payment with secure biometrics and one-time credentials with the system of FIG. 1.
Figure 12:
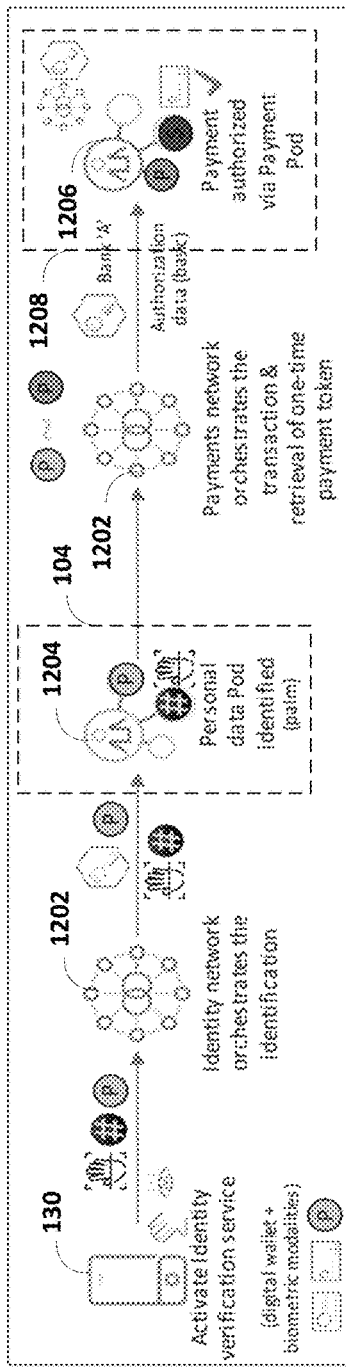

FIG. 12 is flow diagram illustrating examples 1200 and 1250 for payment with secure biometrics and one-time credentials with the system 100 of FIG. 1, in accordance to various aspects of the present disclosure.

In example 1200 of FIG. 12, the local partner device 130 captures the biometrics of the individual 140 and generates a biometric token based on the captured biometrics. In response to generating the biometric token, the local partner device 130 sends the biometric token to the local identity server 104 (e.g., a server administered by a bank) via an identity and payments network 1202.

The local identity server 104 matches the biometric token that is received from the local partner device 130 to a data pod 1204. The local identity server 104 confirms whether authorization to make a payment at the local partner device 130 exists in the data pod 1204 or whether the data pod 1204 includes an identification of payment pod 1206 associated with the individual 140. When the authorization exists in the data pod 1204, the local identity server 104 generates a payment token that approves the transaction at the local partner device 130 and sends the payment token to the local partner device 130 via the identity and payments network 1102.

When the identification of payment pod 1206 associated with the individual 140 exists in the data pod 1204, the local identity server 104 requests payment authorization from the payment pod 1206 via the identity and payments network 1202. In the example of FIG. 12, the payment pod 1206 is located at another server external to the local identity server 104. For example, the payment pod 1206 may be located in a server 1208 of another bank. However, in other examples, the payment pod 1206 may also be located on the local identity server 104 and/or the optional global identity server 118. When the authorization exists in the payment pod 1206, and in response to receiving the payment authorization, the server 1208 generates a payment token that approves the transaction at the local partner device 130 and sends the payment token to the local partner device 130 via the identity and payments network 1202.

In example 1250 of FIG. 12, the individual 140 completes checkout by activating an identity verification service on the local partner device 130 (e.g., an identity verification service application on the individual's smartphone). The local partner device 130 includes a digital wallet, biometric modalities, and a payment credential. The local partner device 130 requests a biometric capture of the individual 140.

The local partner device 130 captures the biometrics of the individual 140 and generates a biometric token based on the captured biometrics. The local partner device 130 verifies the biometric token that is generated matches a pre-existing token stored in the memory of the local partner device 130. In response to verifying the biometric token, the local partner device 130 sends the biometric token and the payment credential to the local identity server 104 (e.g., a server administered by a bank) via an identity and payments network 1202.

The local identity server 104 matches the biometric token that is received from the local partner device 130 to the data pod 1204. The local identity server 104 confirms whether authorization to make a payment at the local partner device 130 exists in the data pod 1204 or whether the data pod 1204 includes an identification of the payment pod 1206 associated with the individual 140. When the authorization exists in the data pod 1204, the local identity server 104 generates a payment token that approves the transaction at the local partner device 130 and sends the payment token to the local partner device 130 via the identity and payments network 1202.

When the identification of payment pod 1206 associated with the individual 140 exists in the data pod 1204, the local identity server 104 requests payment authorization from the payment pod 1206 via the identity and payments network 1202. In the example of FIG. 12, the payment pod 1206 is located at another server external to the local identity server 104. For example, the payment pod 1206 may be located in the server 1208 of another bank. However, in other examples, the payment pod 1206 may also be located on the local identity server 104 and/or the optional global identity server 118. When the authorization exists in the payment pod 1206, and in response to receiving the payment authorization, the server 1208 generates a payment token that approves the transaction at the local partner device 130 and sends the payment token to the local partner device 130 via the identity and payments network 1202.

In summary of FIG. 12, successful biometric authentication leads to a one-time credential or token. Further, the digital data pod may have varying rules. For example, when a facial biometric token is used to authenticate, then only transactions up to $250 may be authorized. However, when a palm biometric token is used to authenticate, then transactions over $250 may be authorized.

Figure 13:
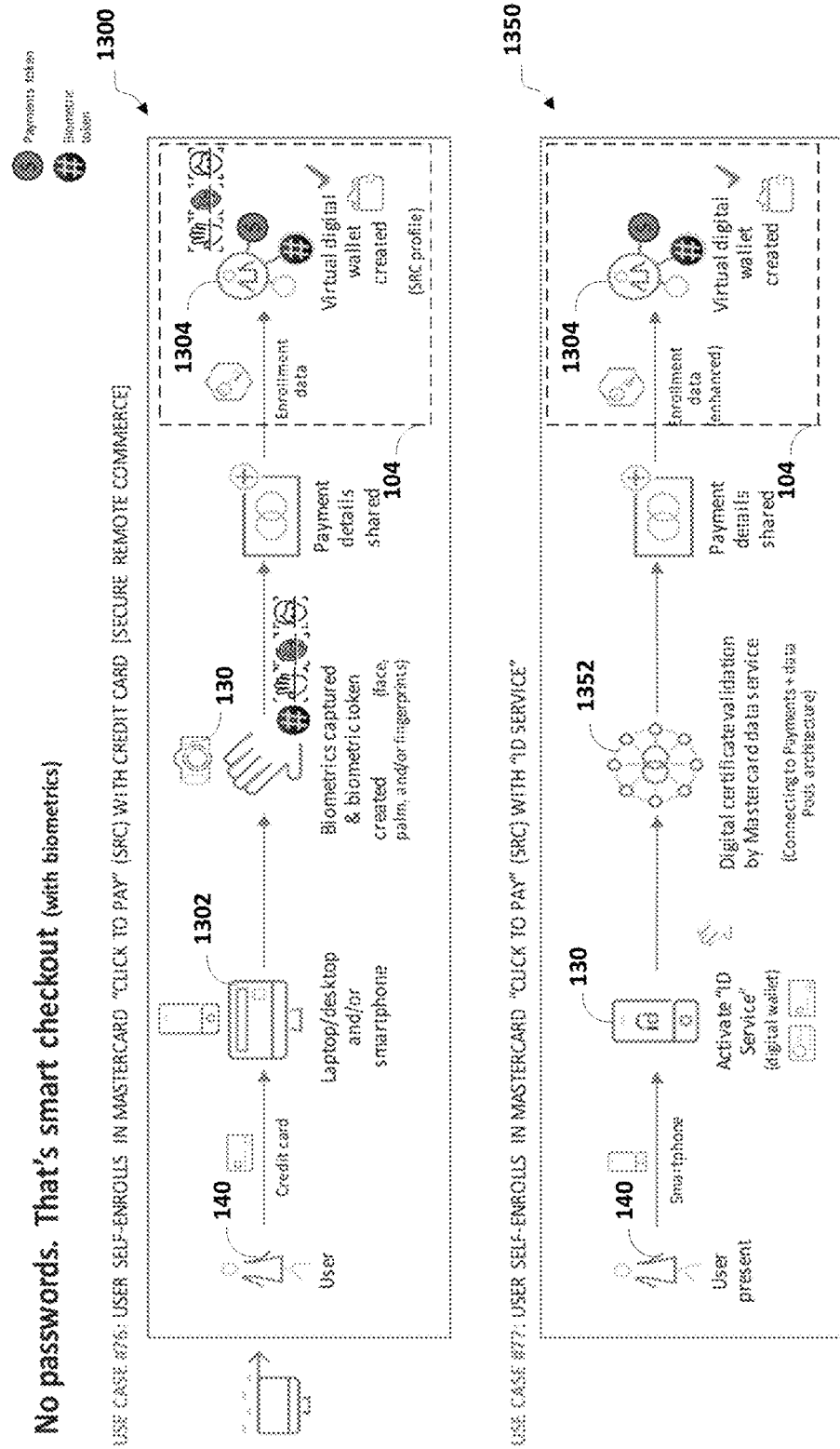
FIG. 13 is flow diagram illustrating examples for smart checkout with the system of FIG. 1.

FIG. 13 is flow diagram illustrating examples 1300 and 1350 for smart checkout with the system 100 of FIG. 1, in accordance to various aspects of the present disclosure.

In example 1300 of FIG. 13, the individual 140 provides a credit card to a computing device 1302 to enroll in click for pay with the credit card. The individual 140 also provides biometrics to the local partner device 130 (e.g., the computing device 1302 or some other suitable computing device that captures biometrics), which captures the biometrics of the individual 140 and generates a biometric token based on the captured biometrics.

In response to generating the biometric token, the local partner device 130 sends the biometric token and the payment details as enrollment data to the local identity server 104 (e.g., a server administered by a bank) via an identity and a payments network. In response to receiving the enrollment data, the local identity server 104 creates a payments pod 1304 including the biometric token and payments token.

In example 1350 of FIG. 13, the individual 140 activates an identity service on the local partner device (e.g., a smartphone) to enroll in click for pay. The individual 140 also provides biometrics to the local partner device 130, which captures the biometrics of the individual 140 and generates a biometric token based on the captured biometrics.

In response to generating the biometric token, the local partner device 130 sends the biometric token and the payment details as enrollment data to the local identity server 104 (e.g., a server administered by a bank) via an identity and payments network 1352. In response to receiving the enrollment data, the local identity server 104 creates a payments pod 1304 including the biometric token and a payments token.

In the example of FIG. 13, the biometric token may be linked to, or inside of, a secure remote commerce (SRC) account. Further, multiple rules may be set in place with respect to the SRC account. For example, when the individual 140 is present, and biometrically authenticated, only then will an online transaction for $10,000+ will go through (limits set by the individual 140).

One primary advantage of the biometric token is an additional level of assurance for some transactions and/or interactions. For example, the biometric token enables cardless payments online, that is, the individual 140 does not need to enter card details. Instead, the individual 140 may simply authenticate biometrically to your SRC account.

Another advantage of the biometric token is an excellent defense against an "account takeover." Moreover, while biometric templates and biometric images may provide a similar defense against an "account takeover," biometric images and biometric templates are very sensitive data and pose a significant risk even when sent encrypted.

The biometric token may still be used to biometrically authenticate the individual 140. However, the biometric token is useless random data to any one that views the biometric token.

Further, there are very few rules in place on transaction size, links to specific and deliberate user agreement (for highest value transactions). Most high value transactions are expected to be carried out via ACH, wire transfer, check, but not often debit cards or credit cards. In other words, the biometric token may provide proof of presence and proof of liveness behind a given SRC transaction.

Yet another advantage is that the biometric tokens will allow the individual 140 to link together different SRC accounts. Conventionally, each SRC implementation is a standalone SRC account. The individual 140 must sign up for more than one SRC account if the individual 140 plans to shop via SRC with more than one payment processor. However, the biometric token may be used to allow the individual 140 to access SRC accounts across all payment processors.

Figure 14:
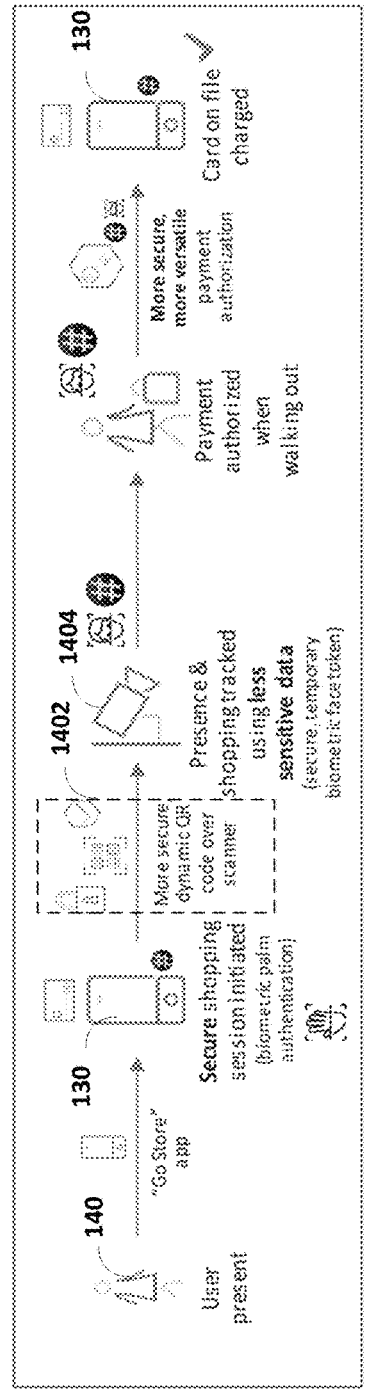
FIG. 14 is flow diagram illustrating examples for checking out using an application versus biometrics only with the system of FIG. 1.
Figure 14:
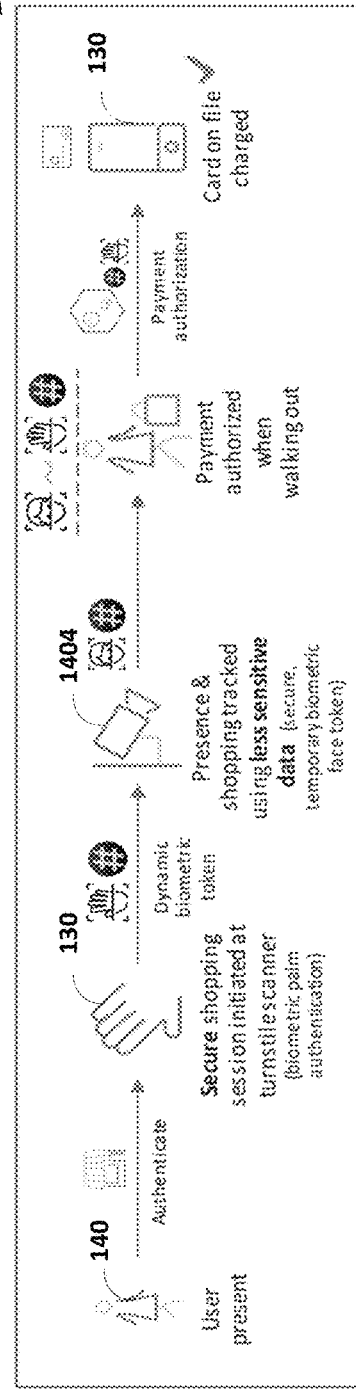

FIG. 14 is flow diagram illustrating examples 1400 and 1450 for checking out using an application versus biometrics only with the system 100 of FIG. 1, in accordance to various aspects of the present disclosure.

In example 1400 of FIG. 14, the individual 140 activates a store application on the local partner device 130 (e.g., a smartphone). The individual 140 also provides biometrics to the local partner device 130, which captures the biometrics of the individual 140 and generates a biometric token based on the captured biometrics.

In response to generating the biometric token, the local partner device 130 authenticates the biometric token to confirm the identity of the individual 140 and generates a dynamic QR code that confirms the use of the store application on the local partner device 130. In response to generating the dynamic QR code, the individual 140 presents the dynamic QR code to a scanner 1402.

In response to scanning the dynamic QR code, the scanner 1402 controls a presence detection device 1404 (e.g., a camera or camera system) to track the presence and shopping of the individual 140 based on the dynamic QR code that points to the shopping application of the local partner device 130. In some examples, the presence detection device 1404 tracks the presence and shopping of the individual 140 by generating a temporary biometric token by scanning the face or other distinguishing body part of the individual 140 and connecting any items retrieved by the individual 140 to the temporary biometric token.

Once the presence detection device 1404 detects the individual 140 leaving the store, the presence detection device 1404 communicates the retrieved items to the scanner 1402 and deletes the temporary biometric token. In response to receiving the retrieved items from the presence detection device 1404, the scanner 1402 charges the local partner device 130 for the retrieved items. In response to receiving a charge from the scanner 1402, the local partner device 130 charges a credit card on file in the store application of the local partner device 130.

In example 1450 of FIG. 14, the individual 140 has previously enrolled in payment authorization with a merchant using a first biometric token. The individual 140 provides biometrics to the local partner device 130 (e.g., a turnstile scanner), which captures the biometrics of the individual 140 and generates a dynamic biometric token based on the captured biometrics. The local partner device 130 confirms the dynamic biometric token authenticates the individual 140 by comparing the dynamic biometric token to the first biometric token.

In response to determining that the individual 140 is authenticated and has previously enrolled in payment authorization, the local partner device 130 controls the presence detection device 1404 (e.g., a camera or camera system) to track the presence and shopping of the individual 140. In some examples, the presence detection device 1404 tracks the presence and shopping of the individual 140 by generating a temporary biometric token by scanning the face or other distinguishing body part of the individual 140 and connecting any items retrieved by the individual 140 to the temporary biometric token.

Once the presence detection device 1404 detects the individual 140 leaving the store, the presence detection device 1404 communicates the retrieved items to the local partner device 130 and deletes the temporary biometric token. In response to receiving the retrieved items from the presence detection device 1404, the local partner device 130 charges a credit card or digital wallet on file from enrollment by the individual 140.

In the example of FIG. 14, the partner does not need to store biometric images or biometric templates in a local or a central ecosystem, which leads to fewer cybersecurity and data privacy risks. Additionally, the example 1400 may use a more "private" biometric modality like a palm scan to initiate and authorize creation of a stronger credential with a higher level of assurance (e.g., for the purpose of entering the store and initiating the purchase experience).

In summary, the local partner device 130 links a palm biometric token (instead of a facial biometric token) to the payment details (stored as a payment token and/or credit card information). The local partner device 130 may bind the palm biometric token from the QR code with the facial biometric token collected at the time of the entrance to the shopping area (e.g., at the turnstile).

The local partner device 130 may use facial recognition technology and the presence detection device 1404 to track purchases and determine when the user is leaving the purchase area. Lastly, the local partner device 130 may retrieve the face to palm link to process a payment.

One advantage of the example 1400 is that the local partner device 130 may an application deployed on any smart device with a regular camera. Another advantage is that the application only uses biometric tokens versus encrypted biometric templates sent to the cloud. Yet another advantage of the example 1400 is a more secure local storage on the mobile device—as the risks associated with biometric tokens are extremely small compared to biometric templates or biometric images—and allows the example 1400 to be deployed in an offline environment when the individual 140 has pre-registered biometrically.

Figure 15:
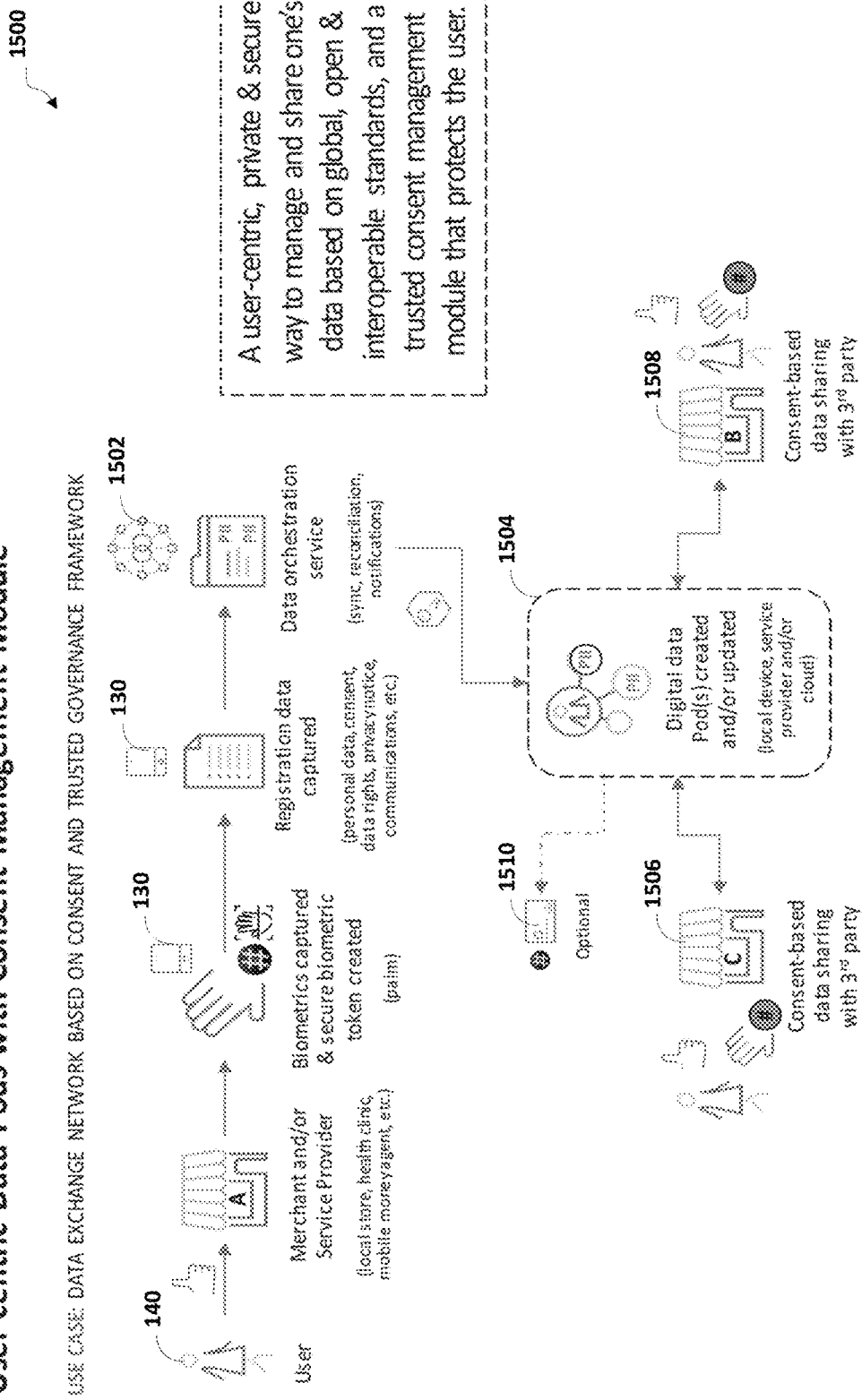
FIG. 15 is flow diagram illustrating an example of creating or updating user-centric data pods with the system of FIG. 1.

FIG. 15 is flow diagram illustrating an example 1500 of creating or updating user-centric data pods with the system 100 of FIG. 1, in accordance to various aspects of the present disclosure.

In example 1500 of FIG. 15, the individual 140 visits a partner and provides biometrics to the local partner device 130, which captures the biometrics of the individual 140 and generates a biometric token based on the captured biometrics. In response to generating the biometric token, the local partner device 130 captures registration data from the individual 140. The registration data may include personal data, consent data rights, one or more privacy notices, communications, payment credentials, or other suitable registration data.

In response to capturing the registration data, the local partner device 130 uses a data orchestration service 1502 to create or update a digital data pod 1504. The digital data pod 1504 may be created and located on any one of the local partner device 130, the local identity server 104, the optional global identity server 118, or some combination thereof. When the digital data pod 1504 is created and located on the local partner device 130, the local partner device 130 may synchronize with the local identity server 104 and/or the optional global identity server 118 to also create and maintain the digital data pod 1504. In some examples, the local partner device 130 may be a smartphone in the possession of the individual 140.

When the digital data pod 1504 is located on the local partner device 130, the local partner device 130 may share data included in the digital data pod 1504 with one or more third-parties 1506 and 1508 when the individual 140 has provided consent to sharing data to third-parties. When the digital data pod 1504 is located on the local identity server 104, the local identity server 104 may share data included in the digital data pod 1504 with one or more third-parties 1506 and 1508 when the individual 140 has provided consent to sharing data to third-parties. When the digital data pod 1504 is located on the optional global identity server 118, the optional global identity server 118 may share data included in the digital data pod 1504 with one or more third-parties 1506 and 1508 when the individual 140 has provided consent to sharing data to third-parties.

Optionally, in some examples, the digital data pod 1504 may be connected to a physical identification or payment card via a biometric token stored in the digital data pod 1504. In these examples, when the digital data pod 1504 also includes payment credentials, then the digital data pod 1504 is also considered a "payment pod" as described herein.

Figure 16:
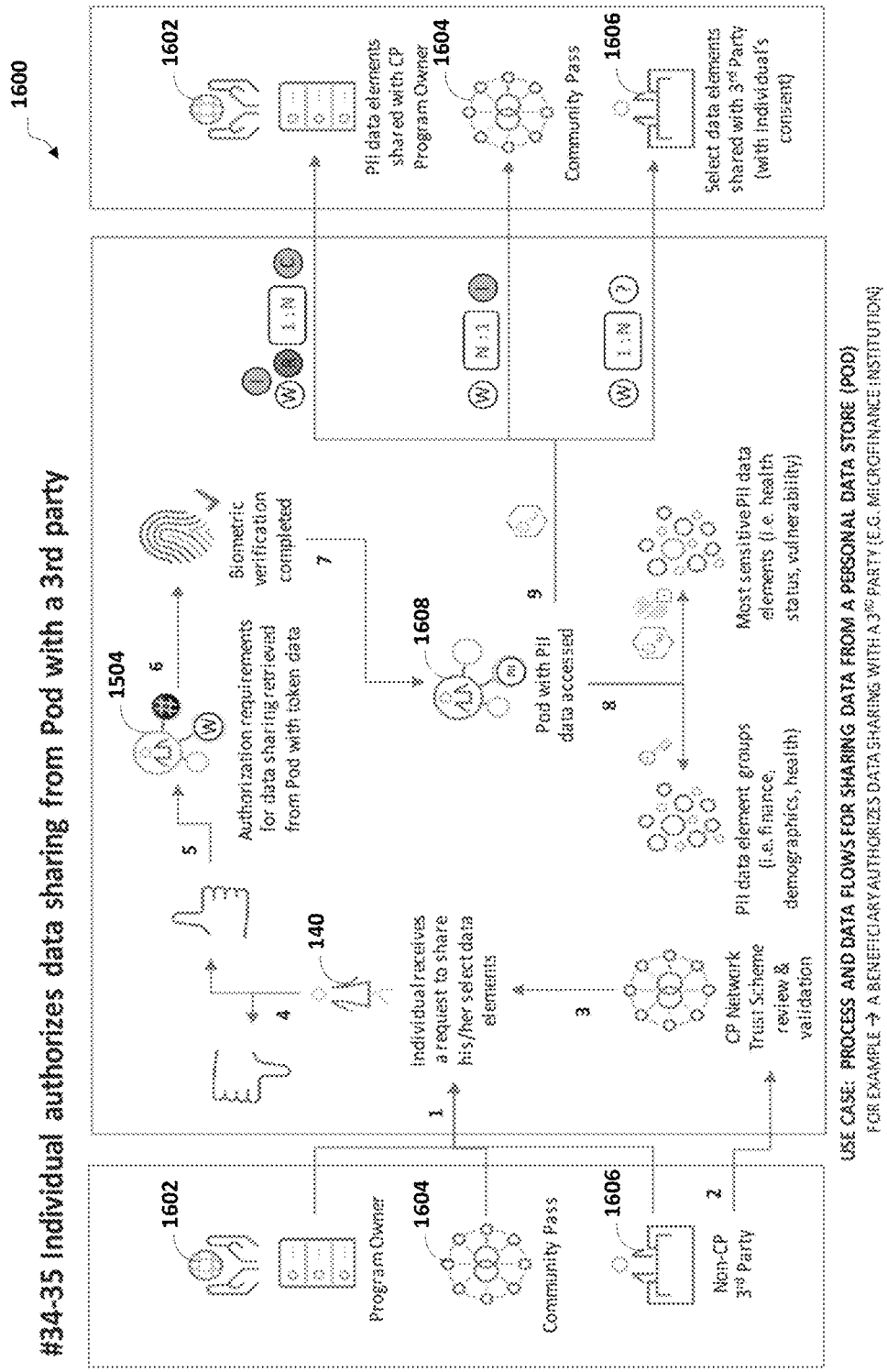
FIG. 16 is flow diagram illustrating an example authorizing data sharing from the digital data pod of FIG. 15 using a consent management module.

FIG. 16 is flow diagram illustrating an example 1600 authorizing data sharing from the digital data pod 1504 of FIG. 15 using a consent management module, in accordance to various aspects of the present disclosure. In the example of FIG. 16, the individual 140 receives a request to share select data elements from a program owner 1602, a community pass third-party 1604, or a non-community pass third-party 1606 (at link 1). When the request comes from the non-community pass third-party 1606, the community pass network trust scheme review validation occurs in parallel to the request to reduce or eliminate spam or fraud (at links 2 and 3).

The individual 140 may deny data sharing to any of the requests (at link 4). The individual 140 may also approve of data sharing to any of the requests (at link 5).

When the individual 140 approves of data sharing (at link 5), the individual 140 must provide biometrics to generate a biometric token. The biometric token that is generated allows a computing device to identify to the digital data pod 1504 that is associated with the individual 140. Upon identifying the digital data pod 1504, the computing device retrieves authorization requirements for data sharing from the digital data pod 1504. When biometric verification is one of the authorization requirements, the computing device may perform biometric verification with the biometric token that was generated and a second biometric token stored with the digital data pod 1504 (at link 6).

Once the computing device has satisfied the authorization requirements, the computing device may either access the PII data from the digital data pod 1504 or retrieve a pointer that points to a PII data pod 1608 that stores PII data of the individual 140. In the example of FIG. 16, after retrieving the pointer, the computing device may access the PII data pod 1608 (at link 7).

Once the computing device has accessed the PII data pod 1608, the computing device may access different types of PII (at link 8). For example, the computing device may access PII data element groups including finance, demographics, and health. The computing device may also access more sensitive PII data including a health status, social security number, vulnerability, or other highly sensitive PII data.

After accessing the PII data in the PII data pod 1608, the computing device may share any PII data elements with the community pass program owner 1602 (at link 9). The computing device may share only some of the PII data elements with the community pass third-party 1604 (at link 9). Lastly, the computing device may share only select PII data elements with a non-community pass third-party 1606 with the consent of the individual 140 (at link 9).

A digital existence of the individual 140 needs the ability to share data (verified & unverified) with respective service providers. This data may reside at different service providers (i.e., health, utility, bank, etc.). The example 1600 provides the individual 140 control and only the individual 140 may authorize such exchange of data (unless another person has been authorized by the individual 140), and reduces or eliminates any violation of the privacy of the individual 140. The example 1600 addresses the disadvantages of conventional sharing of data because the conventional sharing of this data with new service providers is visible to all parties involved and also prone to man-in-the-middle attacks or other similar attacks.

Figure 17:
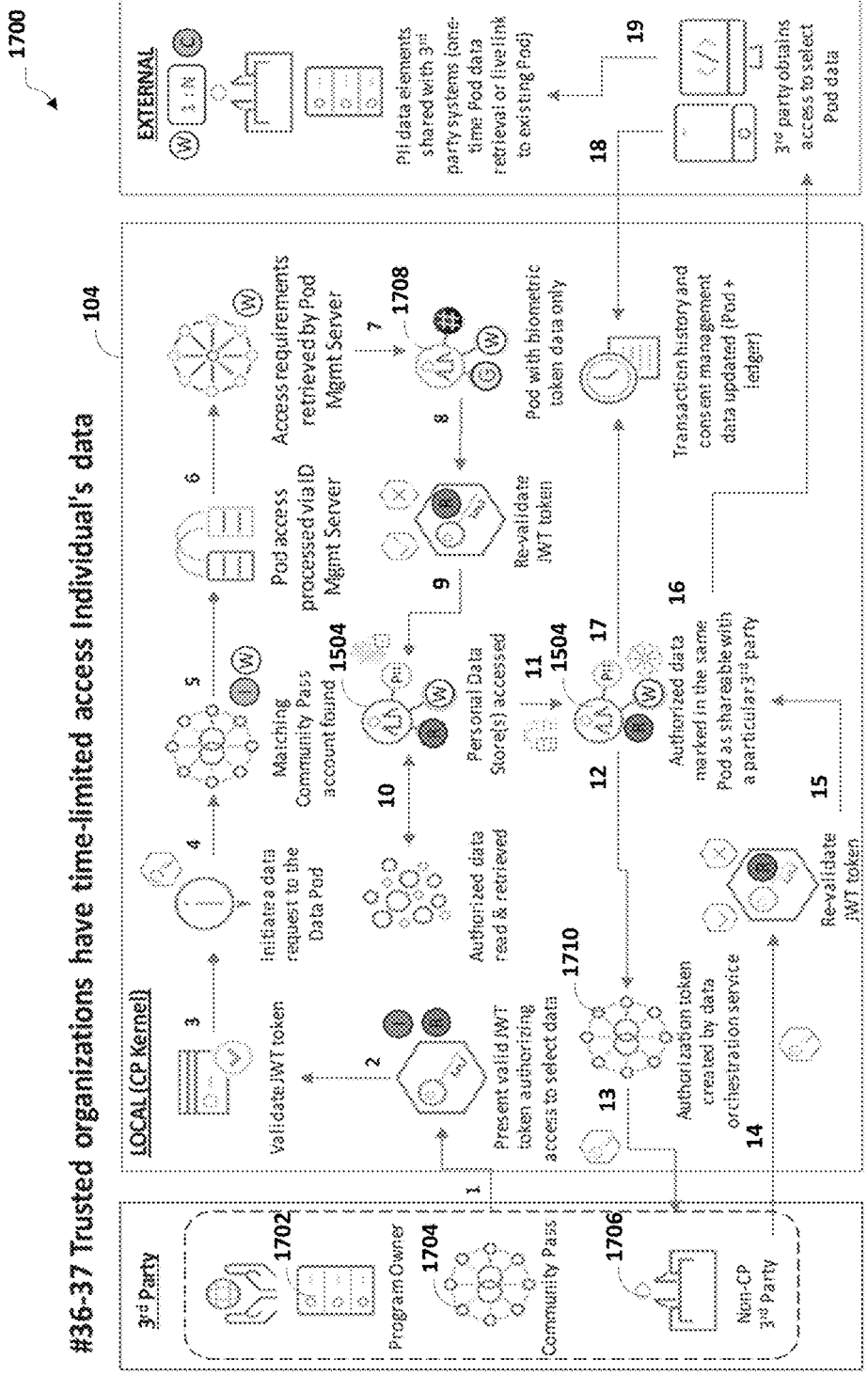
FIG. 17 is flow diagram illustrating an example authorizing time-limited data sharing from the digital data pod of FIG. 15 using a consent management module.

FIG. 17 is flow diagram illustrating an example 1700 authorizing time-limited data sharing from the digital data pod 1504 of FIG. 15 using a consent management module, in accordance to various aspects of the present disclosure.

In the example of FIG. 17, one of third-parties 1602-1606 presents a JSON-web token the local identity server 104 authorizing access to select data elements of the digital data pod 1504 (at link 1). The local identity server 104 validates the JSON-web token (at link 2). In response a validating the JSON-web token, the local identity server 104 initiates a data request to a digital data pod 1708 (at link 3). In response to initiating the data request, the local identity server 104 matches and finds a community pass account (i.e., the digital data pod 1708) (at link 4). After finding the community pass account, the local identity server 104 initiates the identity management service to process pod access (at link 5).

Additionally, the local identity server 104 executes a pod management service to retrieve access requirements (at link 6). In the example of FIG. 17, the local identity server 104 determines that the digital data pod 1708 is a biometric data pod with biometric token data only (at link 7). After determining that the data pod 1708 is a biometric data pod with the biometric token data only, the local identity server 104 re-validates the JSON-web token (at link 8).

After re-validating the JSON-web token, the local identity server 104 accesses the authorized data in the digital data pod 1504 with a relationship identifier that was included the digital data pod 1708 (at link 9). After accessing the authorized data, the local identity server 104 reads and retrieves the authorized data from the digital data pod 1504 (at link 10). Additionally, the local identity server 104 marks the authorized data in the digital data pod 1504 as shareable with the specific third-party requesting the authorized data (at link 11). After marking the authorized data as shareable to the specific third-party in the digital data pod 1504, the local identity server 104 executes a digital orchestration service 1710 to create and send an authorization token to one or more of the third-parties 1702-1706 (at link 12).

One or more of the third-parties 1702-1706 re-send the JSON-web token back to the local identity server 104 for re-validation along with the authorization token that includes the relationship identifier that identifies the digital data pod 1504 (at link 14). The local identity server 104 enables access to the one or more of the third-parties 1702-1706 in the digital data pod 1504 (link 15). After enabling access, the one or more third-parties gain access to the select pod data that is marked as shareable with the one or more third-parties 1702-1706 (at link 16).

Additionally, in parallel or subsequent to the one or more third-parties 1702-1706 obtaining access to the select pod data, a transaction history and content management data is updated in a ledger stored in the digital data pod 1504 by the local identity server 104 and the one or more third-parties 1702-1706 that accessed the digital data pod 1504 (at links 17 and 18). Lastly, access to the select pod data shared with the one or more third-parties 1702-1706 is either ended as a one-time link or continued as a live link to the digital data pod 1504 (at link 19).

In summary, with respect to the example 1700, only the individual 140 may authorize the use of their data and only the recipient or requester may see the data that is requested and authorized. The provider of the data cannot track the activity of the individual 140 and the network is blind the contents of the data that is requested and authorized.

Figure 18:
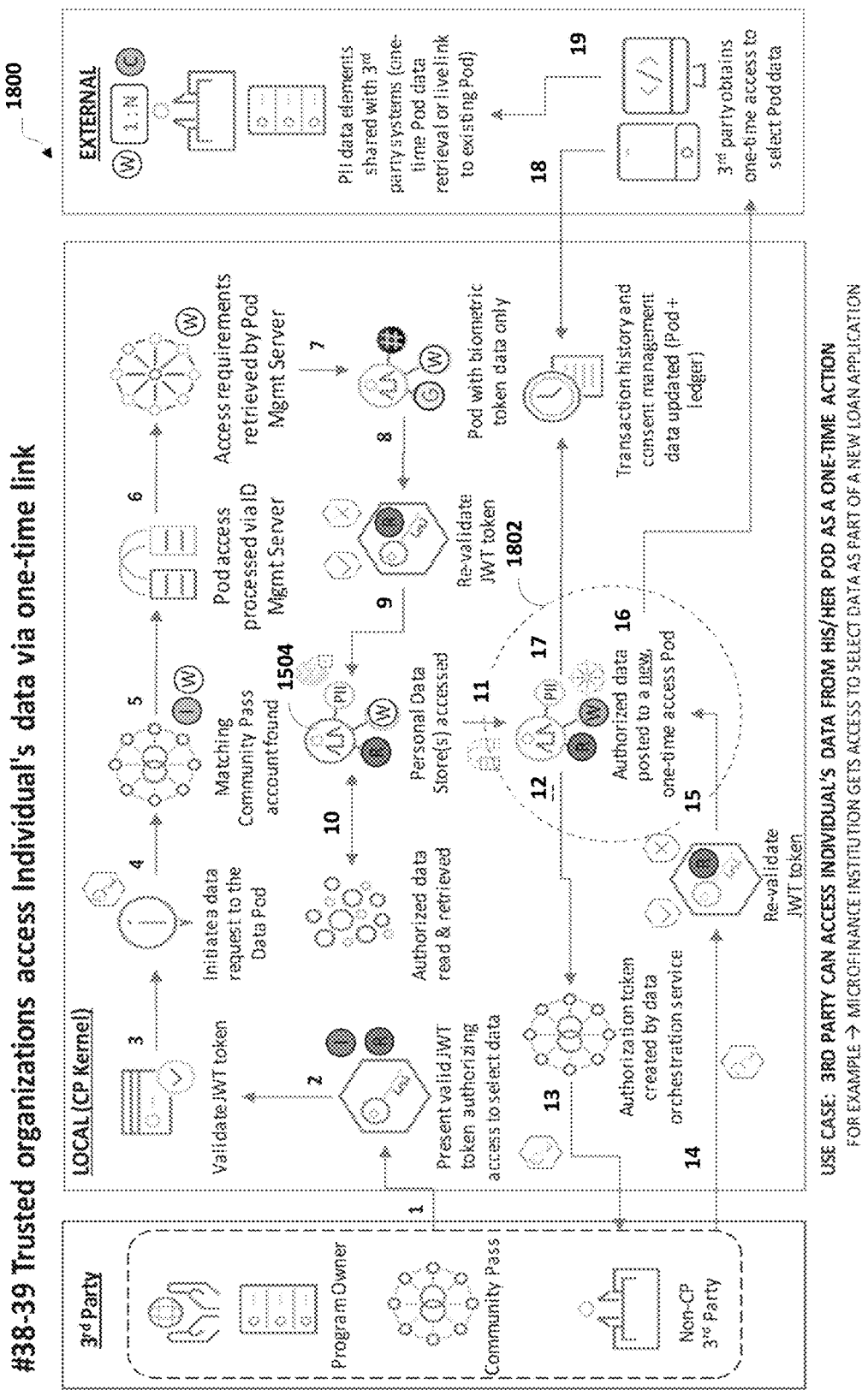
FIG. 18 is flow diagram illustrating an example authorizing time-limited data sharing from the digital data pod of FIG. 15 using a consent management module.

FIG. 18 is flow diagram illustrating an example 1800 authorizing time-limited data sharing from the digital data pod 1504 of FIG. 15 using a consent management module, in accordance to various aspects of the present disclosure. FIG. 18 is similar to FIG. 17. Consequently, any redundant description is not repeated herein.

The difference between FIGS. 17 and 18 is a difference between allowing third-parties to access the digital data pod 1504 directly with one-time access or continuous access versus allowing third-parties to access a new, one-time digital data pod 1802 that may have a set expiration. For example, the one-time digital data pod 1802 may expire after a single access, after a set period of time, or other suitable expiration scheme. In other words, the difference between FIGS. 17 and 18 is the creation of a temporary digital data pod 1802.

In summary, with respect to the example 1800, on a successful authorization, a new temporary pod is created on the network. A new one-time encryption key is generated and authorized data is encrypted and stored in the temporary pod. The authorization token along with the encryption key and temporary pod location is sent to the data provider. The data provider writes the data to the temporary pod and encrypts the data. The authorization token, pod location and keys are sent to the requestor. The requestor retrieves the data and decrypts the data.

Additionally, access to sensitive personal data may be enabled via creation of one-time use data pods, which are linked to the main data pod for the individual 140. The data to be shared with a specific entity (approved by the individual 140) is then placed in a temporary data pod and the link is shared with the specific entity to access the data for a limited period of time. After that the data is no longer accessible, and the data pod and its link are destroyed. The link should not be reusable in the future. Alternatively, the access to the data pod could be permanently disabled.

Figure 19:
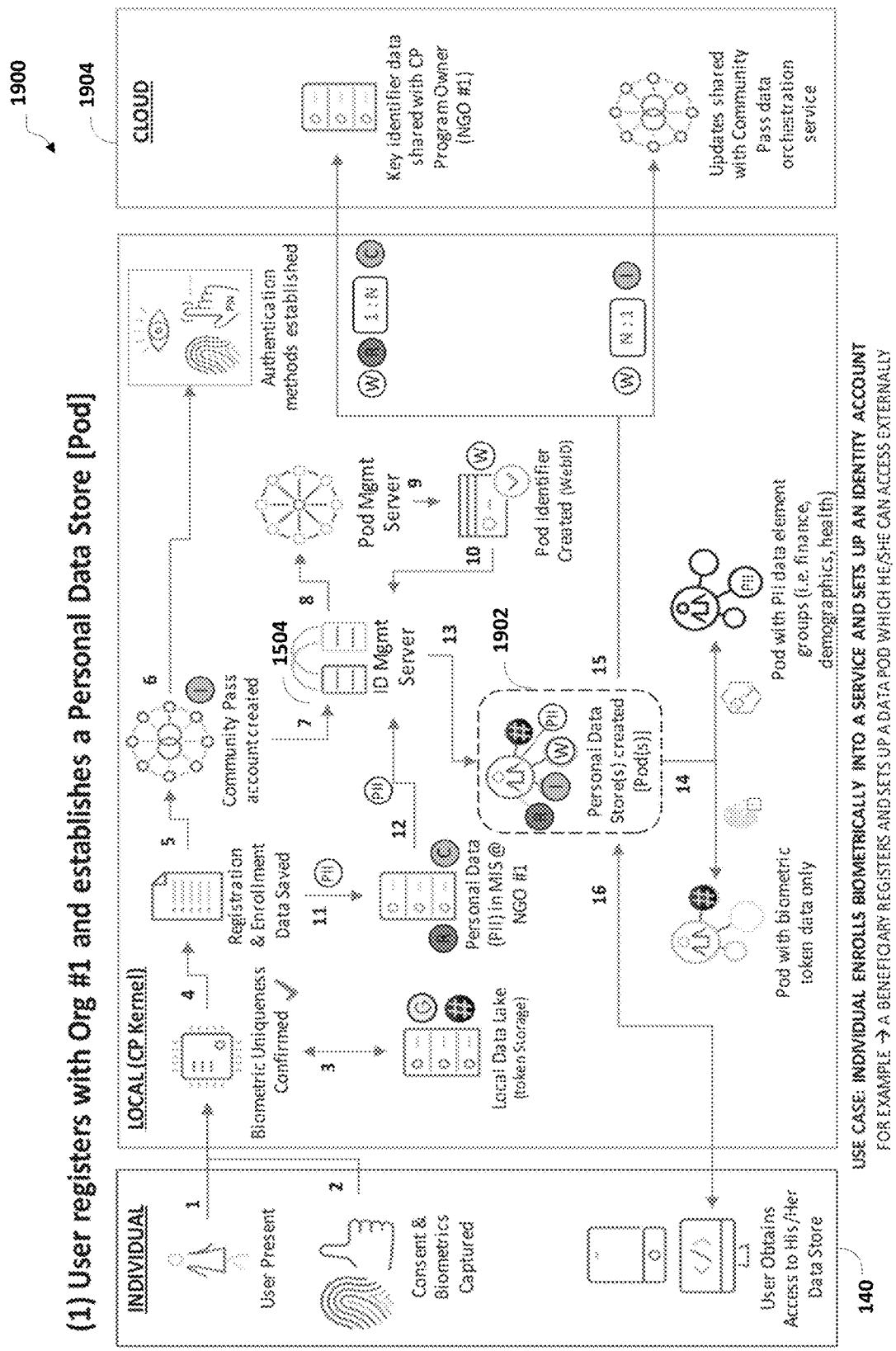
FIG. 19 is flow diagram illustrating an example of an individual registering with a partner and establishing a data pod with the system of FIG. 1.

FIG. 19 is flow diagram illustrating an example 1900 of an individual registering with a partner and establishing a data pod with the system 100 of FIG. 1, in accordance to various aspects of the present disclosure.

In example 1900 of FIG. 19, the individual 140 visits a partner and provides biometrics along with consent to the local partner device 130 (at links 1 and 2). Upon capturing the biometrics of the individual 140, the local partner device 130 generates a biometric token based on the captured biometrics. In response to generating the biometric token, the local partner device 130 confirms the uniqueness of the biometric token in the local biometric token (b-token) storage of the local partner device 130 (at link 3).

In response to confirming the uniqueness of the biometric token, the local partner device 130 stores the biometric token in the local b-token storage and captures registration data from the individual 140 (at links 3 and 4). The local partner device 130 requests the local identity server 104 to create a community pass account (at link 5).

After creating the community pass account, the local identity server 104 establishes authentication methods (at link 6). The local identity server 104 also executes the identity management service and the pod management service to create a data pod identifier (at links 7-9). The local identity server 104 then receives the data pod identifier (at link 10).

Additionally, in parallel to requesting the local identity server 104 to create the community pass account, the local partner device 130 stores the PII data locally (at link 11). After storing the PII data locally, the local partner device 130 also sends the PII data to the local identity server 104, and in particular, for receipt by the identity management service (at link 12).

In response to receiving both the data pod identifier and the PII data, the local identity server 104 creates a personal data store 1902 (also referred to as a personal data pod) (at link 13). The personal data store 1902 the PII data, the biometric token, and the pod identifier.

Additionally, in the example of FIG. 19, the local identity server 104 also creates to sub-pods: a first sub-pod that includes only the biometric token and points back to the personal data store 1902 and a second sub-pod with only the PII data (at link 14). After creating the sub-pods, the local identity server 104 provides the pod identifier and the community pass account identifier to the cloud 1904, and specifically, as an update shared with the community pass orchestration service 1906 (at link 15). Additionally, after creating the sub-pods, the local identity server 104 provides the pod identifier, the relationship identifier, and a service credential to the cloud 1904, and specifically, as key identifier data shared with the partner (i.e., the community pass program owner) (at link 15). Lastly, the local identity server 104 provides access of the personal data store 1902 to the individual 140 (at link 16).

In summary, with respect to the example 1900, every organization that the individual 140 interacts with may create data pods specific to the individual and under the complete control of the individual 140. After successful biometric authentication, the individual 140 may choose to vail of such personal storage of all or selective data of their interactions. This data pod may then be accessed by the individual 140 at a later time to access and/or share the data with other providers. All access to such data pods is biometrically authenticated and recorded prior to any access or sharing.

Figure 20:
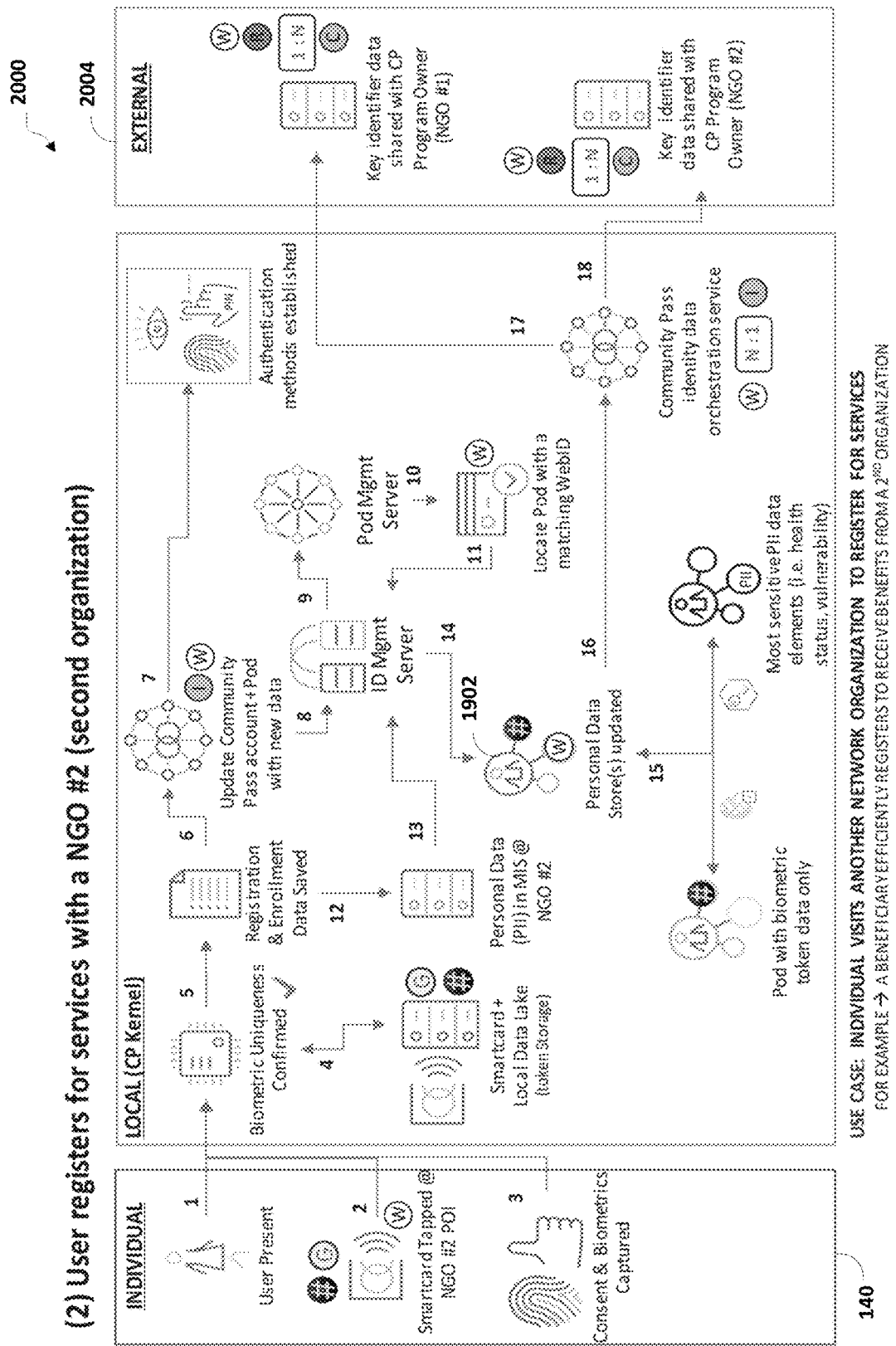
FIG. 20 is flow diagram illustrating an example of an individual registering with another partner and updating a data pod with the system of FIG. 1.

FIG. 20 is flow diagram illustrating an example 2000 of an individual registering with another partner and updating a data pod with the system 100 of FIG. 1, in accordance to various aspects of the present disclosure. FIG. 20 is similar to FIG. 19. Consequently, any redundant description is not repeated herein.

The difference between FIGS. 19 and 20 is a difference between an account creation versus an account update. The individual 140 created a community pass account and the personal data store 1902 in FIG. 19. In the example of FIG. 20, the individual 140 provides a smart card to a second partner, where the smartcard identifies the personal data store 1902 with a pod identifier and includes a biometric token and a GUID. The local identity server 104 updates the community pass account and the personal data store 1902 to include new data, specifically, a new biometric token and new PII data (link 14). The local identity server 104 also updates the cloud 2004 by providing key identifier data to the first partner described in FIG. 19 (at link 17) and to the second partner described in FIG. 20 (at link 18). The key identifier data may include the pod identifier, a relationship identifier, and a service credential.

With respect to the example 2000, a previously enrolled user and PII data are shared with the new service provider. The example 2000 uses the biometrics tokens to track consent and authorization to pod data.

Figure 21:
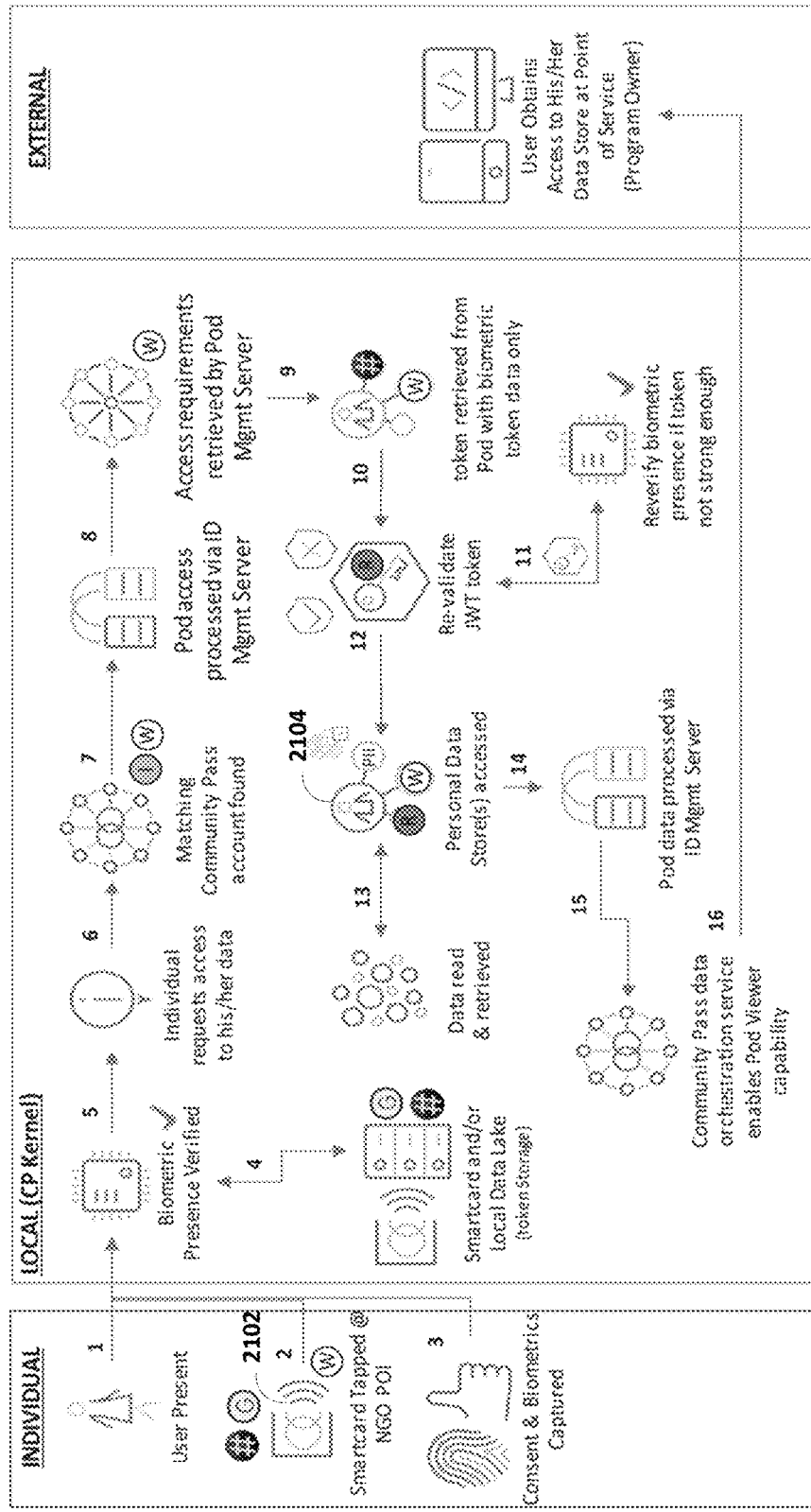
FIG. 21 is flow diagram illustrating an example of an individual accessing a data pod at a point of service with the system of FIG. 1.

FIG. 21 is flow diagram illustrating an example 2100 of an individual accessing a data pod at a point of service with the system 100 of FIG. 1, in accordance to various aspects of the present disclosure.

In the example of FIG. 21, the individual 140 provides consent to a biometrics capture to a local partner device 130 (at links 1 and 3). The individual 140 may also provide a smartcard 2102 that is ready by the local partner device 130 of the partner (at link 2). The smartcard 2102 may include a first biometric token, a GUID, and a pod identifier. The local partner device 130 may verify that the individual 140 is the owner of the smartcard 2102 by generating a second biometric token from the captured biometrics and comparing it to the first biometric token (at link 1). The local partner device 130 may store the first and second biometric tokens, the GUID, and the pod identifier in local storage (at link 4).

The individual 140 may request access data stored in a data pod associated with the individual 140 (at link 5). The local partner device 130 may send a partner identifier and the pod identifier to the local identity server 104 to find a community pass account (at link 6). After finding the community pass account, the local identity server 104 may process pod access by executing an identity management service (at link 7). After executing the identity management service, the local identity server 104 retrieves access requirements from the pod management service (at link 8).

In the example of FIG. 21, a JSON-web token validation may be the access requirement for accessing the data pod. As illustrated in FIG. 21, the JSON-web token is retrieved from the biometric data pod that only includes biometric token data (at link 9). The local identity server 104 re-validates the JSON-web token (at link 10).

When the re-validation of the JSON-web token is not strong enough, then the local identity server 104 may request the local partner device 130 to re-verify the biometric presence of the individual 140 (at link 11). When the re-validation of the JSON-web token is strong enough, the local identity server 104 accesses the personal data store 2104 (at link 12). The local identity server 104 reads and retrieves the requested pod data from the personal data store 2104 (at link 13).

The local identity server 104 processes the pod data with the identity management service (at link 14). After processing the pod data with the identity management service, the local identity server 104 enables pod viewer capability via the community pass data orchestration service (at link 15). The individual 140 obtains access to the pod data at the point of service by viewing the pod data via the community pass data orchestration service (at link 16).

In summary, with respect to the example 2100, service providers may store transaction data and PII data in user-specific pods. The access to these user-specific pods are controlled and protected by biometric tokens from registration by the individual 140. The biometric tokens for matching will stored in the user-specific pod and allows the individual 140 to authenticate to the pod and manage their data.

Figure 22:
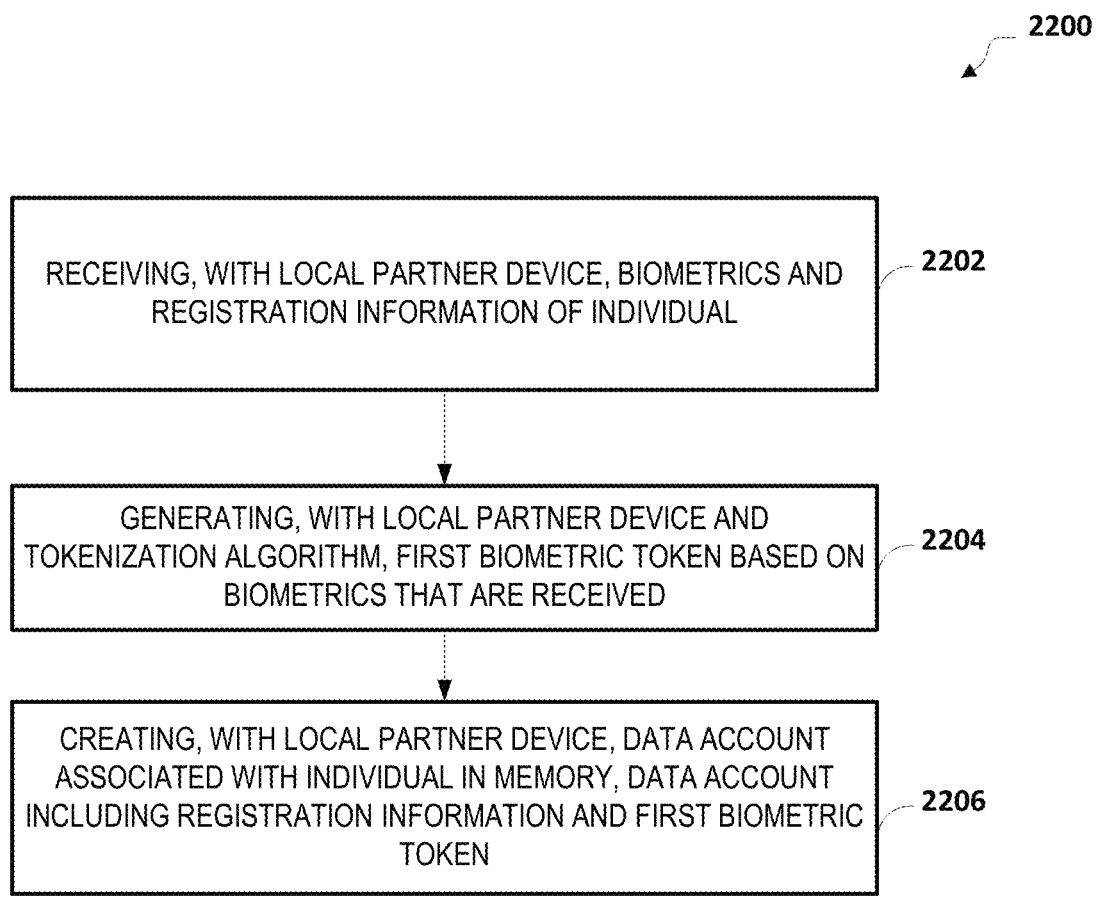
FIG. 22 is flow diagram illustrating an example process for securely storing information of an individual.

FIG. 22 is flow diagram illustrating an example process 2200 for securely storing information of an individual, in accordance with various aspects of the present disclosure. FIG. 22 is described with respect to FIG. 1.

In the example of FIG. 22, the method 2200 includes receiving, with a local partner device 130, biometrics and registration information of an individual 140 (at block 2202). The method 2200 includes generating, with the local partner device 130 and a tokenization algorithm, a first biometric token based on the biometrics that are received (at block 2204). The method also includes creating, with the local partner device 130, a data account associated with the individual 140 in a memory, the data account including the registration information and the first biometric token (at block 2206). Lastly, the first biometric token is different from a biometric image or a biometric template in that the first biometric token only matches a copy of the first biometric token or a second biometric token that is generated from a second set of the biometrics of the individual 140 with the tokenization algorithm.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure. It should thus be noted that the matter contained in the above description or shown in the accompanying drawings is to be interpreted as illustrative and not in a limiting sense.

What is claimed is:

1. A system for securely storing information of an individual, the system comprising:
   a local partner device including a first electronic processor, a first communication interface, and a first memory, the first electronic processor is configured to
     receive biometrics and registration information of an individual,
     generate, with a tokenization algorithm, a first biometric token based on the biometrics that are received, and
     create a data account associated with the individual in the first memory, the data account including the registration information and the first biometric token,
   wherein the first biometric token is different from a biometric image or a biometric template in that the first biometric token only matches a copy of the first biometric token or a second biometric token that is generated from a second set of the biometrics of the individual with the tokenization algorithm.

2. The system of claim 1, wherein the first electronic processor is further configured to create a second data account associated with the individual in the first memory, the second data account including only the copy of the first biometric token that links the second data account to the data account.

3. The system of claim 1, further comprising:
   a local identity server including a second electronic processor, a second communication interface, and a second memory, the second electronic processor is configured to
   receive the data account from the local partner device, and
   create a distributed data account associated with the individual in the second memory, the distributed data account including the registration information and the first biometric token.

4. The system of claim 3, wherein the second electronic processor is further configured to create a second data account associated with the individual in the second memory, the second data account including only the copy of the first biometric token that links the second data account to at least one of the data account or the distributed data account.

5. The system of claim 1, further comprising:
   a plurality of local partner devices, each including a second electronic processor, a second communication interface, and a second memory,
   wherein the first electronic processor is further configured to control the first communication interface to synchronize the data account with the plurality of local partner devices, and
   wherein each of the plurality of local partner devices is configured to create a distributed data account associated with the individual in a third memory, the distributed data account including the first biometric token and the registration information stored in the data account.

6. The system of claim 5, wherein the second electronic processor is further configured to create a second data account associated with the individual in the second memory, the second data account including only the copy of the first biometric token that links the second data account to at least one of the data account or the distributed data account.

7. The system of claim 1, wherein the data account expires after a set period of time, and wherein the first electronic processor is configured to
   delete the data account after an expiration of the set period of time, or
   permanently disable the data account after the expiration of the set period of time.

8. The system of claim 1, wherein the first electronic processor is further configured to
   receive an input from the individual that revokes consent of the individual with respect to the data account
   receive the second set of the biometrics of the individual;
   generate the second biometric token from the second set of the biometrics of the individual that is received;
   identify the individual and the data account by matching the second biometric token that is generated to the first biometric token that is stored in the data account, and delete the data account or permanently disable the data account in response to receiving the input and identifying the data account.

9. A method for securely storing information of an individual, the method comprising:
receiving, with a local partner device, biometrics and registration information of an individual;
generating, with the local partner device and a tokenization algorithm, a first biometric token based on the biometrics that are received; and
creating, with the local partner device, a data account associated with the individual in a memory, the data account including the registration information and the first biometric token,
wherein the first biometric token is different from a biometric image or a biometric template in that the first biometric token only matches a copy of the first biometric token or a second biometric token that is generated from a second set of the biometrics of the individual with the tokenization algorithm.

10. The method of claim 9, further comprising:
creating, with the local partner device, a second data account associated with the individual in the memory, the second data account including only the copy of the first biometric token that links the second data account to the data account.

11. The method of claim 9, further comprising:
receiving, with a local identity server, the data account from the local partner device; and
creating, with the local identity server, a distributed data account associated with the individual in a second memory, the distributed data account including the registration information and the first biometric token.

12. The method of claim 11, further comprising:
creating, with the local identity server, a second data account associated with the individual in the second memory, the second data account including only the copy of the first biometric token that links the second data account to at least one of the data account or the distributed data account.

13. The method of claim 9, further comprising:
controlling, with the local partner device, a first communication interface to synchronize the data account with a plurality of local partner devices, and
wherein each of the plurality of local partner devices is configured to create a distributed data account associated with the individual in a third memory, the distributed data account including the first biometric token and the registration information stored in the data account.

14. The method of claim 13, wherein the each of the plurality of local partner devices is further configured to create a second data account associated with the individual in a second memory, the second data account including only the copy of the first biometric token that links the second data account to at least one of the data account or the distributed data account.

15. The method of claim 9, wherein the data account expires after a set period of time, the method further comprising:
deleting, with the local partner device, the data account after an expiration of the set period of time, or
permanently disabling, with the local partner device, the data account after the expiration of the set period of time.

16. The method of claim 9, further comprising:
receiving, with the local partner device, an input from the individual that revokes consent of the individual with respect to the data account;
receiving, with the local partner device, the second set of the biometrics of the individual;
generating, with the local partner device, the second biometric token from the second set of the biometrics of the individual that is received;
identifying, with the local partner device, the individual and the data account by matching the second biometric token that is generated to the first biometric token that is stored in the data account; and
deleting or permanently disabling, with the local partner device, the data account in response to receiving the input and identifying the data account.

17. A non-transitory computer-readable medium comprising instructions that, when executed by an electronic processor, cause the electronic processor to perform a set of operations comprising:
receiving, with a local partner device, biometrics and registration information of an individual;
generating, with the local partner device and a tokenization algorithm, a first biometric token based on the biometrics that are received; and
creating, with the local partner device, a data account associated with the individual in a memory, the data account including the registration information and the first biometric token,
wherein the first biometric token is different from a biometric image or a biometric template in that the first biometric token only matches a copy of the first biometric token or a second biometric token that is generated from a second set of the biometrics of the individual with the tokenization algorithm.

18. The non-transitory computer-readable medium of claim 17, wherein the set of operations further includes
controlling a first communication interface to synchronize the data account with a plurality of local partner devices, and
wherein each of the plurality of local partner devices is configured to create a distributed data account associated with the individual in a third memory, the distributed data account including the first biometric token and the registration information stored in the data account.

19. The non-transitory computer-readable medium of claim 17, wherein the data account expires after a set period of time, the set of operations further includes
deleting the data account after an expiration of the set period of time, or
permanently disabling the data account after the expiration of the set period of time.

20. The non-transitory computer-readable medium of claim 17, further comprising:
receiving an input from the individual that revokes consent of the individual with respect to the data account;
receiving the second set of the biometrics of the individual;
generating the second biometric token from the second set of the biometrics of the individual that is received;
identifying the individual and the data account by matching the second biometric token that is generated to the first biometric token that is stored in the data account; and deleting or permanently disabling the data account in response to receiving the input and identifying the data account.

\* \* \* \* \*